US006762294B2

(12) United States Patent
Goldman et al.

(10) Patent No.: US 6,762,294 B2
(45) Date of Patent: Jul. 13, 2004

(54) POLYNUCLEOTIDES ENCODING POLYMORPHIC HUMAN GABAA RECEPTOR α-6 SUBUNIT

(75) Inventors: David Goldman, Potomac, MD (US); Nakao Iwata, Aichi (JP); Marc A. Schuckit, Del Mar, CA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 208 days.

(21) Appl. No.: 09/930,589

(22) Filed: Aug. 15, 2001

(65) Prior Publication Data

US 2003/0138776 A1 Jul. 24, 2003

Related U.S. Application Data

(63) Continuation of application No. PCT/US00/04189, filed on Feb. 18, 2000.
(60) Provisional application No. 60/120,812, filed on Feb. 19, 1999.

(51) Int. Cl.$^7$ ............................ C07H 21/04; C12Q 1/68
(52) U.S. Cl. ............................................. 536/23.5; 435/6
(58) Field of Search ........................ 536/23.5; 530/300, 530/350; 435/6

(56) References Cited

FOREIGN PATENT DOCUMENTS

| WO | 94/13799 | 6/1994 |
| WO | 99/00389 | 1/1999 |

OTHER PUBLICATIONS

Burt, D. R. and Kamatchi, G. L. (1991) GABA$_A$ receptor subtypes: from pharmacology to molecular biology. FASEB J. 5:2916–2923.
Ciraulo, D. A., et al. (1989) Parental Alcoholism as a Risk Factor in Benzodiazepine Abuse: A Pilot Study. Am. J. Psychiatry 146:1333–1335.
Cloninger, C. R., et al. (1981) Inheritance of Alcohol Abuse. Arch. Gen. Psychiatry 38:861–868.
Cowley, D. S., et al. (1992) Response to Diazepam in Sons of Alcoholics. Alcohol. Clin. Exp. Res. 16(6):1057–1063.
Cowley, D. S., et al. (1994) Eye Movement Effects of Diazepam in Sons of Alcoholic Fathers and Male Control Subjects. Alcohol. Clin. Exp. Res 18(2):324–332.
Deitrich, R. A., et al. (1989) Mechanism of Action of Ethanol: Initial Central Nervous System Actions. Pharmacol. Rev. 41(4):489–537.

Hadingham, K. L., et al. (1996) Cloning of cDNAs Encoding the Human γ–Aminobutyric acid Type A Receptor α6 Subunit and Characterization of the Pharmacology of α6–Containing receptors. Mol. Pharmacol. 49:253–259.
Iwata, N., et al. (1999) Relationship Between a GABA$_A$ α6 Pro385Ser Substitution and Benzodiazepine Sensitivity. Am. J. Psychiatry 156(9):1447–1449.
Iwata, N., et al. (1999) GABA$_A$ α6 polymorphisms and relationship to benzodiazepine sensitivity. (Abstract) Biol. Psychiatry Suppl. 45:82S
Iwata, N., et al. (2000) Identification of a naturally occuring Pro385–Ser385 substitution in the GABA$_A$ receptor α6 subunit gene in alcoholics and healthy volunteers. Mol. Psychiatry 5:316–319.
Korpi, E. R., et al. (1993) Benzodiazepine–induced motor impairment linked to point mutation in cerebellar GABA$_A$ receptor. Nature 361:356–359.
Luddens, H., et al. (1990) Cerebellar GABA$_A$ receptor selective for a behavioural alcohol antagonist. Nature 346:648–651.
Pollock, V. E. (1992) Meta–Analysis of Subjective Sensitivity to Alcohol in Sons of Alcoholics. Am. J. Psychiatry 149:1534–1538.
Radel, M., et al. (1998) Detection of Sequence Variants in GABA$_A$ Receptor Subunit Genes by DHPLC Analysis. (Abstract) (Alcohol Clin. Exp. Res. 22(3):98A.
Schuckit, M. A., et al. (1999) Selective Genotyping for the Role of 5–HT$_{2A}$, 5–HT$_{2C}$, and GABA$_{\alpha 6}$ Receptors and the Serotonin Transporter in the Level of Response to Alcohol: A Pilot Study, Biol. Psychiatry 45:647–651.
Schuckit, M. A. (1988) Reactions to Alcohol in Sons of Alcoholics and Controls. Alcohol Clin. Exp. Res. 12(4): 465–470.
Schuckit, M. A., et al. (1991) Subjective Feelings and Changes in Body Sway Following Diazepam in Sons of Alcoholics and Control Subjects. J. Stud. Alcohol 52(6):601–608.
Sigel, E. and Buhr, A. (1997) The benzodiazepine binding site of GABA$_A$ receptors. TiPS 18:425–429.

*Primary Examiner*—Robert Landsman
(74) *Attorney, Agent, or Firm*—Knobbe, Martens, Olson & Bear LLP

(57) ABSTRACT

Compositions and methods based on a polymorphism in the gene encoding the α6 subunit of the human GABA$_A$ neurotransmitter receptor are disclosed. This polymorphism results in the substitution of a serine residue for a proline residue ordinarily present at amino acid position 385 of the α6 polypeptide sequence. Significantly, the polymorphism was associated with decreased sensitivity to ethanol and benzodiazepine drugs.

4 Claims, No Drawings

POLYNUCLEOTIDES ENCODING POLYMORPHIC HUMAN GABAA RECEPTOR α-6 SUBUNIT

CROSS-REFERENCE TO RELATED APPLICATIONS

This application is a continuation of International Application number PCT/US00/04189 and claims the benefit of priority of International Application No. PCT/US00/04189 having international filing date Feb. 18, 2000, designating the United States of America and published in English, which claims the benefit of priority of U.S. application Ser. No. 60/120,812 filed Feb. 19, 1999; both of which are hereby expressly incorporated by reference in their entireties.

FIELD OF THE INVENTION

The present invention relates generally to the field of molecular genetics. More particularly, the invention relates to a polynucleotide sequence encoding a variant α6 subunit of the human $GABA_A$ neurotransmitter receptor, the sequence variant predicting sensitivity to both benzodiazepine drugs and ethanol.

BACKGROUND OF THE INVENTION

Human heritability studies using twins and adoptees have indicated that alcoholism is a complex disorder having a genetic component. (Hesselbrock, "The Genetic Epidemiology of Alcoholism" in *The Genetics of Alcoholism*, Edited by Begleiter H, Kissin B. New York, Oxford University Press, pp 17–39 (1995)). Sons of alcoholics (SOAs) are a group at high risk for developing alcoholism (Cloninger et al., *Arch Gen Psychiatry* 38:861 (1981)), and so have been the focus of numerous studies on the subjective, psychomotor, physiological and biochemical responses to ethanol. (Schuckit, *Alcohol Clin Exp Res* 12:465 (1988); Newlin et al., *Psychol Bull* 108:383 (1990); Pollock, *Am J Psychiatry* 149:1534 (1992)). These studies have identified several differences between SOAs and male control subjects which can provide clues to the basis of increased risk of developing alcoholism.

One of the distinctions between SOAs and male control subjects relates to differential sensitivity to benzodiazepine drugs (BZD) and ethanol. More particularly, SOAs have been shown to be significantly less sensitive to BZD (Ciraulo et al., *Am J Psychiatry* 146:1333 (1989); Cowley et al., *Alcohol Clin Exp Res* 16:1057 (1992); Cowley et al., *Alcohol Clin Exp Res* 18:324 (1994)) and ethanol (Schuckit et al., *Arch Gen Psychiatry* 53:202 (1996)) when compared with male control subjects. The genetic and neurobiological mechanisms underlying this diminished sensitivity is unclear, because these drugs affect multiple neurotransmitter systems in the central nervous system. (CNS) (Deitrich et al., *Pharmacol Rev* 41:489 (1989)).

γ-Aminobutyric acid (GABA) is a key inhibitory neurotransmitter in the mammalian CNS. GABA subtype A ($GABA_A$) receptors are chloride channels that specifically bind benzodiazepine drugs with high affinity (Luddens et al., *Neuropharmacology* 34:245 (1995)) to result in chloride ion influx. Molecular analysis has revealed that $GABA_A$ receptor channels are heterooligomeric structures composed of several distinct polypeptide subunits (α1–6, β1–3, γ1–3, and δ). (Burt et al., *FASEB J* 5:2916 (1991)).

Two lines of evidence have implicated the $GABA_A$ receptor in differential sensitivity to alcohol. First, cerebellar membranes of "ANT" and "AT" rats exhibited differential affinity for BZD. (Uusi-Oukari et al., *J Neurochem* 54:1980 (1990)). The Alcohol-sensitive ANT (Alcohol Non-Tolerant) and alcohol-insensitive AT (Alcohol Tolerant) lines of rats have been selectively bred to exhibit differences in sensitivity to ethanol-induced motor impairment. An amino acid substitution Arg100Glu in the $GABA_A$ α6 receptor is believed to be at least partially responsible for the difference in alcohol sensitivity which characterizes these two rat lines. The alcohol insensitive AT line carries the Arg100 form of the receptor and is diazepam insensitive when compared with the Glu100 $GABA_A$ α6 receptor. (Korpi et al., *Nature* 361:356 (1993)).

In a second line of evidence, the $GABA_A$ γ2 subunit was implicated in the differential sensitivity of long-sleep (LS) and short-sleep (SS) mouse lines to acutely administered alcohol. (Wafford et al., *Science* 249:291 (1990)). An in vitro mutagenesis and expression system employing Xenopus oocytes was used to demonstrate that alternative RNA splicing of a region of the $GABA_A$ γ2L subunit, which encodes a consensus protein kinase C (PKC) phosphorylation site, was critical for modulation by ethanol. (Wafford et al., *Neuron* 7:27 (1991); Wafford et al., *FEBS Lett* 313:113 (1992)). Clearly there remains a need to better understand the genetic basis for differential sensitivity to benzodiazepine drugs and alcohol in humans.

SUMMARY OF THE INVENTION

Compositions and methods based on a polymorphism in the gene encoding the α6 subunit of the human $GABA_A$ neurotransmitter receptor are disclosed. This polymorphism results in the substitution of a serine residue for a proline residue ordinarily present at amino acid position 385 of the $GABA_A$ α6 polypeptide sequence. In a first set of experiments, we demonstrate that patients having the Pro385Ser polymorphism exhibit a reduced sensitivity to diazepam, a benzodiazepine drug known in the art to mimic a subject's response to ethanol, when compared with patients having the proline residue at amino acid position 385. The Pro385Ser polymorphism was found to be associated with less change in smooth pursuit eye movement gain after intravenous diazepam was administered to children of alcoholics (COAs). In a second set of experiments, we demonstrate that patients having the Pro385Ser polymorphism exhibit a reduced sensitivity to ethanol when compared with patients having the proline residue at amino acid position 385. Thus, the polymorphism was associated with decreased sensitivity to ethanol and benzodiazepine drugs.

DETAILED DESCRIPTION OF THE INVENTION

Herein, we have discovered two genetic differences or "polymorphisms" that occur in the gene sequence encoding the α6 subunit of the human $GABA_A$ neurotransmitter receptor. In the most prevalent form of the α6 subunit of the human $GABA_A$ neurotransmitter receptor, a proline residue is present at amino acid position 385 given by the sequence provided by Hadingham et al., *Mol Pharmacol* 49(2):253–259 (1996), herein incorporated by reference. This form of the α6 receptor subunit protein or the α6 receptor subunit protein-encoding polynucleotide having a proline residue at amino acid position 385 is referred to throughout this disclosure as "Pro385".

In this invention, we have discovered a first polymorphism, called "Pro385Ser" or "Ser385", in the α6 subunit of the human GABA$_A$ neurotransmitter receptor. This form of the α6 subunit of the human GABA$_A$ neurotransmitter receptor is characterized by a substitution of a serine residue for the proline residue which is ordinarily present at amino acid position 385. In some contexts, the term "Pro385Ser" or "Ser385" refers to a polymorphism in a polynucleotide encoding α6 protein (in which case the polymorphism is with reference to codon 385 of the α6-encoding polynucleotide), or to the α6 protein itself (in which case the polymorphism is with reference to amino acid position 385 of the α6 polypeptide sequence given by Hadingham et al., *Mol Pharmacol* 49(2):253–259 (1996). In other contexts, the term Pro385Ser or Ser385 refers to a polymorphism in a polynucleotide encoding a fragment of α6 protein (in which case the polymorphism is with reference to codon 385 of the α6 fragment-encoding polynucleotide), or to a fragment of the α6 protein itself (in which case the polymorphism is with reference to amino acid position 385 of the α6 polypeptide sequence given by Hadingham et al., *Mol Pharmacol* 49(2):253–259 (1996). The Pro385Ser polymorphism can also be referred to as GABRA6 1236C>T to indicate the single nucleotide change at position 1236 which confers the substitution of the serine amino acid residue for the proline amino acid residue at amino acid position 385.

We have also discovered a second polymorphism, called G1031C, but this nucleotide change did not alter the amino acid sequence of the α6 receptor. The G1031C polymorphism can also be referred to as GABRA6 1031G>C.

The Pro385Ser polymorphism occurs within a portion of the α6 subunit of the human GABA$_A$ neurotransmitter receptor corresponding to the second intracellular domain of the receptor near a putative protein kinase C phosphorylation site. By the phrase, "a portion of the α6 subunit of the human GABA$_A$ neurotransmitter receptor" is meant a segment of the α6 polypeptide sequence that includes at least 50–100 amino acids, more preferably at least 20 contiguous amino acids, and even more preferably at least 3, 6 or 10 contiguous amino acids. The Pro385Ser polymorphism exhibits a rarer-allele frequency of 0.08, whereas, the G1031C polymorphism exhibits a rarer-allele frequency of 0.47. By "Allele" or "allelic variant" is meant the natural polynucleotide sequences corresponding to polymorphisms present in human beings.

In the following disclosure, we first demonstrate that patients having the Pro385Ser polymorphism exhibit a reduced sensitivity to diazepam, a benzodiazepine drug known in the art to mimic a subject's response to ethanol, when compared with patients having the proline residue at amino acid position 385. The Pro385Ser polymorphism was found to be associated with less change in smooth pursuit eye movement gain after intravenous diazepam was administered to children of alcoholics (COAs). In contrast, the G1031C polymorphism did not correlate with diazepam sensitivity. Second, we demonstrate that patients having the Pro385Ser polymorphism exhibit a reduced sensitivity to ethanol when compared with patients having the proline residue at amino acid position 385.

Biological tools, therapeutics, and methods of use of the foregoing are provided. Further, embodiments that employ diagnostics or diagnostic kits, which are particularly useful for the rapid identification of the Pro385Ser polymorphism and, thus the determination of the relative sensitivity to a BZD drug or ethanol in an individual having a particular genotype, are provided. In the section below, we discuss the discovery of the Pro385Ser polymorphism in greater detail. Genetic Polymorphisms in the GABA$_A$ Receptor α6 Subunit Those having ordinary skill in the art will appreciate that differential sensitivity to benzodiazepine drugs is a useful indicator of brain differences correlating with behavioral variation, including susceptibility to alcoholism. In rats, for example, variation in alcohol and benzodiazepine sensitivity has been correlated with an inherited variant of the GABA$_A$ α6 receptor. Significantly, responses to eye movement tasks which can be measured as saccade gain, peak saccade velocity, and smooth pursuit gain, have been demonstrated to be reliable and reproducible within and between testing sessions, and to be objective, quantifiable measures affected by BZD in a dose-dependent manner. (Roy-Byrne et al., *Psychopharmacology* 110:85–91 (1993); Roy-Byrne et al., *Biol Psychiatry* 38:92 (1995)). Accordingly, in the procedures described below, eye movement testing provided a convenient means of monitoring BZD and ethanol sensitivity in human subjects.

Based on the finding that SOAs exhibited decreased sensitivity to BZD, and the fact that rodent genetic studies implicated GABA$_A$ receptors in response to BZD and alcoholism, we first investigated whether polymorphisms in the GABA$_A$ α6 subunit gene were associated with differences in BZD sensitivity in children of alcoholics. The procedures employed during the development of the invention involved correlating BZD sensitivity and genotype. More particularly, the procedures involved assessing sensitivity to diazepam in COAs using two eye movement tasks: peak saccadic velocity and average smooth pursuit gain. Genetic variation within the GABA$_A$ α6 receptor gene coding region was evaluated in 56 unrelated COAs by the single strand conformational polymorphism method. Association analysis using a Ser385 substitution, the synonymous variant G1031C and GABA$_A$ α6 haplotype was performed with smooth pursuit gain and peak saccadic velocity as dependent variables. As indicated below, the Ser385 genotype correlated with less diazepam-induced impairment in average smooth pursuit gain (t=1.954, df=53, p=0.04), but not peak saccadic eye velocity. The synonomous G1031C polymorphism was not associated with altered diazepam effects on either eye movement task.

Subjects in the studies described herein were 26 unrelated sons and 30 daughters of alcoholic fathers. All subjects were Caucasian. Subjects ranged from 18–25 years of age. Psychiatric disorders were diagnosed by DSM-III-R criteria and using the Structured Clinical Interview for DSM-III-R (SCID). (Spitzer et al., Structured Clinical Interview for DSM-III-R Patients Edition (SCID-P, 9/1/89 version), New York, Biometrics Research Department New York Psychiatric Institute, (1989)). The proband and at least one first-degree relative were interviewed with the Family Informant Schedule and Criteria. (Mannuzza et al., *Family Informant Schedule and Criteria (FISC)* Anxiety Disorders Clinic, New York, New York Psychiatric Institute, 1985), an extended version of the Family History-Research Diagnostic Criteria (Andreasen et al., *Arch Gen Psychiatry* 43:421 (1986)) and with the Family History Assessment Module from the SSAGA, a structured diagnostic interview used in the Collaborative Study on the Genetics of Alcoholism. (Bucholz et al., *J Stud Alcohol* 55:149 (1994)).

The modalities described above enabled us to confirm the diagnosis of alcohol dependence in the father, how many other first- and second-degree relatives were affected, and to establish family history of other psychiatric disorders. COAs were free of lifetime DSM-III-R Axis I or Axis II psychiatric or substance use disorders, except adjustment disorder and had no history of antisocial personality disorder. All COAs were medically healthy and by their report had taken no medication for at least one month nor had they used a benzodiazepine more than once. All subjects had negative urine drug screens, normal γ-glutamyltransferase, and normal mean corpuscular volume. Example 1 describes the methods that were used to measure BZD sensitivity in human subjects in greater detail. In the section below, we describe the association of diazepam sensitivity with the Pro385 and Ser385 polymorphisms.

Diazepam Sensitivity and the Pro385 or Ser385 GABA$_A$ α6 Genotype

Initially, the saccadic eye movement velocity and smooth pursuit eye movement gain was measured in the 56 COAs tested. Two baseline measurements for each variable were taken and averaged. The differences from this baseline were then evaluated at set time points after each of four diazepam doses. The data points were used to determine, by a trapezoidal technique, the integrated area under the resulting curve. The area under the curve for the dependent variable was then divided by the area under the curve for plasma diazepam levels to correct for individual variability in diazepam levels. The ratios of the areas under the curves for COAs with the Ser385 homozygous genotype and the Pro/Ser heterozygous genotype were then compared by t-test. There were no Ser/Ser homozygotes in the test population of COAs. For the G1031C genotype, a one-way ANOVA was used for assessing association.

The genotypes at each locus were also tested for Hardy-Weinberg equilibrium by Fisher's Exact Test. A maximum likelihood method was used to estimate haplotype frequencies in the double heterozygotes. (Hill, *Heredity* 33:229 (1974); Weir, *Genetic data analysis II*, Sunderland, Mass., Sinauer Associates (1996)). Haplotype frequencies from single heterozygotes were determined by direct counting. Normalized linkage disequilibrium (Δ) and linkage disequilibrium (D) were calculated using these haplotype frequencies.

The polymorphic variation in the GABA$_A$ α6 coding region from the 56 unrelated COAs was then confirmed using SSCP followed by DNA sequencing. (See Example 2). The two relatively abundant polymorphisms that were identified in the α6 coding region are presented in Table 4 (Table 4 can be found in Example 2, infra). A thymidine to cytosine transition at nucleotide 1236 of the coding sequence was identified and the transition results in a substitution of a proline residue by a serine residue at codon 385. This polymorphism was designated "Pro385Ser" or "GABRA6 1236C>T. The second polymorphism identified was a silent G to C substitution at nucleotide 1031, and was designated "G1031C" or GABRA6 1031G>C. As presented in the appended sequence listing, the Pro385 sequence is given by SEQ ID NO: 11, and the Ser385 sequence is given by SEQ ID NO: 12. The G1031C GABA$_A$ α6 sequence is given by SEQ ID NO: 13 while the C1031C sequence is given by SEQ ID NO: 14.

PCR-RFLP assays were also used to facilitate rapid genotyping based on the two GABA$_A$ α6 polymorphisms. (See Example 2). All subjects genotyped by SSCP-analysis and PCR-RFLP yielded identical results. The frequencies of the rarer Pro385Ser and 1031C alleles in the COAs were 0.08 and 0.47, respectively. Both genotype distributions were consistent with expectations based on Hardy-Weinberg equilibrium estimates. The level of linkage disequilibrium between Pro385Ser and G1031C was significant (Δ=1.00, D=0.0401, $\chi^2$=10.8, d.f.=1, p<0.0005).

An association between Ser385 genotype and average smooth pursuit eye movement gain following intravenous diazepam administration was observed (t=1.95, df=53, P=0.04). (See Table 1). COAs having the Pro385Ser allele exhibited a reduced sensitivity to diazepam relative to a group consisting of COAs having the Pro385 genotype. By reduced sensitivity" is meant that a level of sensitivity that is lower than the level of sensitivity which characterizes individuals having the Pro385 genotype. The Pro385Ser allele, however, was not associated with the peak velocity of saccadic eye movement (t=0.171, df=52, p=0.865). Further, no association between the synonymous G1031C polymorphism and either of the two eye movement tasks was found. The numbers of subjects used in the two analyses differed because one individual was so sensitive to diazepam that data for saccadic velocity could not be collected at the highest diazepam dose.

TABLE 1

Association Between Diazepam Sensitivity and the Ser 385 and G1031C Genotypes in COAs

| | Movement | | Task | |
|---|---|---|---|---|
| Eye | Peak saccadic | | | |
| Genotype | n | velocity (SD) | n | smooth pursuit gain* (SD) |
| Pro385Ser | | | | |
| Pro/Pro | 45 | 0.3657 (0.1862) | 46 | 0.5280 (0.2461) |
| Pro/Ser | 9 | 0.3774 (0.1950) | 9 | 0.3602$^a$ (0.1665) |
| Ser/Ser | 0 | | 0 | |
| G1031C | | | | |
| G/G | 12 | 0.3691 (0.1544) | 12 | 0.5093 (0.2078) |
| G/C | 31 | 0.3688 (0.2036) | 32 | 0.5290 (0.2592) |
| C/C | 11 | 0.3629 (0.1802) | 11 | 0.4079 (0.2194) |

$^a$t-test t-value = 1.952, df = 53, p = 0.04
*multiplied by 1000

Next, we looked to correlate polymorphic variants of the GABA$_A$ α6 receptor in COAs, specifically the Ser385 genotype, with saccadic eye movement velocity and smooth pursuit eye movement gain differences in COAs before and after diazepam administration, as disclosed in the section below.

The Pro385Ser Polymorphism and Benzodiazepine/Ethanol Insensitivity

Among the 13 subunits comprising the GABA$_A$/BZD receptor complexes in mammals the α6 subunit is unique in its benzodiazepine agonist-insensitive pharmacology and in its restricted distribution. (Burt et al., *FASEB J* 5:2916 (1991)). GABA$_A$ α6 expression, for example, is limited to cerebellar granule cells. (Luddens et al., *Neuropharmacology* 34:245 (1995); Luddens et al., *Nature* 346:648 (1990)). In the genotyping procedure discussed above, we found that the level of response to alcohol in humans correlated with the GABA$_A$ α6 genotype. This discovery is the first indication that a difference in human diazepam response, and, thus, ethanol response can arise from a naturally occurring variant in a GABA$_A$ receptor subunit. Not wanting to be limited to any particular mechanism and offered only for the purposes of explanantion, we believe that diazepam binding to the α6 Ser385 receptor modulates GABA$_A$ currents, which results in the differences in smooth pursuit eye movement gain observed between subjects having the Pro385 genotype.

We did not observe an association between the Ser385 genotype and saccadic eye movement. Saccadic eye movements involve the parietal cortex, the frontal cortex and associated connections with the basal ganglia, as well as the superior colliculus and, finally, pre-motor areas in pons. (Henn et al., *Rev Neurol* 145:540 (1989)). Pursuit eye movements that were associated with Pro385Ser are predominantly mediated by multiple cortical areas and cerebellum. (Leigh et al., *The Neurology of Eye Movement.* 2 ed. Philadelphia, F. A. Davis Co., 1991). Hence, saccadic velocity and smooth pursuit gain provide a measure of BZD effects in brainstem and cortex/cerebellum, respectively. It is noteworthy that the association of Pro385Ser to pursuit eye movements but not to saccadic movements corresponds to the restricted expression of $GABA_A$ α6 to the cerebellum.

We also did not find any association between G1031C and diazepam sensitivity in spite of the fact that Pro385Ser and G1031C are in strong linkage disequilibrium. Although linkage disequilibrium between the two loci is strong, allele frequency differences between the two loci can account for lack of association with the more abundant G1031C synonymous variant.

Pro385 is conserved in the $GABA_A$ α6 receptors of rats and mice (Luddens et al., *Nature* 346:648 (1990)) (Kato, *J Mol Biol* 214:619 (1990)). The Ser385 amino acid residue is located in the second intracellular domain of the receptor and at a site ten amino acid residues removed from a consensus phosphorylation site for PKC. (Luddens et al., *Nature* 346:648 (1990)). Some believe that the domain can contribute to subtype specificity and intracellular regulatory mechanisms. (Olsen et al., *FASEB J* 4:1469 (1990)). Until the present disclosure, however, a function for this amino acid and domain has not been confirmed.

With respect to the $GABA_A$ γ2L subunit, it is of interest that an alternatively spliced variant of γ2 which contains an extra eight amino acids bears a consensus site for phosphorylation by PKC. (Whiting et al., *Proc Natl Acad Sci USA* 87:9966 (1990)). Site-directed mutagenesis of the alternatively spliced sequence indicates that the γ2L subunit must be phosphorylated to confer ethanol sensitivity. (Wafford et al., *Neuron* 7:27 (1991); Wafford et al., *FEBS Lett* 313:113 (1992)). Not wanting to be limited to any particular mechanism and offered only for the purposes of explanation, we speculate that a similar role for this domain of the α6 subunit could enable the Pro385Ser variant to alter the sensitivity of the receptor to ethanol and BZD.

After determining that individuals with the Pro385Ser polymorphism exhibited a reduced sensitivity to benzodiazepine drugs when compared with patients having the Pro385 polymorphism, we verified that individuals with the Pro385Ser polymorphism also exhibited a reduced sensitivity to ethanol when compared with patients having the wild-type polymorphism. These results are described in the following section.

Individuals with the Pro385Ser Polymorphism Exhibit a Reduced Sensitivity to Ethanol Alcohol abuse and dependence (alcoholism) are complex disorders that appear to reflect several genetic influences that together might explain 40% to 60% of the variance of risk. (Kendler et al., *Arch Gen Psychiatry* 54:178–184 (1997); Pickins et al., *Arch Gen Psychiatry* 48:19–28 (1991)). A low level of response (LR) to alcohol appears to be one route by which vulnerability is mediated. Even after controlling for other influences, LR is apparently both genetically influenced and associated with an enhanced risk for alcohol dependence. Schuckit and Smith, *Arch Gen Psychiatry* 53:202–210 (1996)). In humans, LR has been found to occur at a higher frequency among young drinking, but nonalcoholic, family history positive (FHP) men (Pollock *Am J Psychiatry* 149:1534–1538 (1991); Schuckit and Smith 1996; Newlin and Thomson *Psychol Bull* 108:383–402 (1990)), while identical twins are more similar on LR than fraternal twins. (Madden et al 1995; Rose et al 1994). Three follow-ups of subjects from alcohol challenges have revealed higher rates of alcoholism, alcohol-intake, or problems for individuals with low LR. (Rodriguez et al., *Alcohol Clin Exp Res* 17:155–161 (1993); Schuckit and Smith (1996); Volovka et al *Arch Gen Psychiatry* 53:258–263 (1996)). In addition, our group has reported a correlation for LR of 0.3 across two generations of subjects. Animal studies support the contention that genetic influences impact on LR (Crabbe et al. *J Pharmacol Exp Ther* 277:624–632 (1996)), and in some studies, rodents with low LR have been noted to consume higher amounts of alcohol. (Gill et al., *Alcohol Clin Exp Res* 21:106A (1997); Li et al., *Behavior Genetics* 23:163–170 (1993)).

As part of a larger study, 41 men, about 39 years old, were selected from among the first 113 completed 15-year follow-ups in a prospective study. The genotyping was performed selectively from the first group of consecutively ascertained sons of alcoholics and controls from among what will eventually be a larger population as part of an ongoing study. Seventeen subjects whose low level of response to ethanol (LR) at age 20 were in the lower third were compared on five polymorphisms of four genes with 24 men whose reactions to alcohol had been above the median. Fourteen men with the LL genotype of the serotonin transporter (5-HTT) polymorphism and seven men with the Ser385 genotype of the $GABA_A$ (α6) polymorphism were found to have demonstrated lower LR scores at about age 20 and were significantly at greater risk of alcoholism than the other genotypes for those loci. All four subjects with combined LL and Ser385 genotypes had developed alcoholism and demonstrated the lowest LR scores overall. There was no evidence that two polymorphisms of the $5-HT_{2A}$ receptor gene and one of the $5-HT_{2C}$ receptor gene were related to LR or alcoholism in this sample.

For this pilot study, blood samples were taken from the first 41 appropriate consecutive men among the first 113 who completed 15-year follow-ups in an ongoing study. In order to identify subjects who were clearly low on LR, the men were selected to represent the two poles of LR. These included the first 17 subjects who upon original alcohol challenge at about age 20 demonstrated an overall LR in the lowest third, and the 24 whose intensities of reaction to alcohol had been above the median (High LR). The alcohol challenges, evaluated changes from baseline for subjective feeling of intoxication, standing steadiness, and hormones after drinking 0.75 ml/kg of ethanol. (Schuckit and Gold, *Arch Gen Psychiatry* 45:211–216 (1986). The overall LR was evaluated as the change from baseline (pre-alcohol) to the time of peak blood alcohol concentration (BAC) (60 minute values) following alcohol consumption.

Previously, about ten years after initial testing, all 453 original subjects were located, and 450 (99.3%) were successfully evaluated (Schuckit and Smith 1996). The current pilot data were gathered as part of the ongoing 15-year follow-up of the same sample. For genotyping, blood was drawn at the time of the 15-year interview, and analyses performed blind to the phenotypic classification of the subjects. Five polymorphisms were genotyped from genomic DNA prepared from lymphoblastoid cell lines as follows. For 5HT2a T102C and His452Tyr, using methods described elsewhere, polymorphisms were typed by PCR and restriction enzyme assays (Ozaki et al., *Biol Psychiatry* 40:1267–1272 (1996)). 5HT2c Cys23Ser was genotyped by creating an artificial restriction site using a PCR primer that introduces a base substitution close to the codon of interest (Haliassos et al., *Nucleic Acids Res.* 17:3606 (1989)), and for 5HTTLPR, DNA amplification was accomplished using the two flanking primers used by Heils et al. (*J. Neurochem* 66:2621–2624 (1996)). This set of primers amplifies a 484 or 528 bp fragment corresponding to the 5HTTLPR short or long allele. The Ser385 polymorphism was genotyped using primers GABAaα6-9f and GABAaα6-9b: 5'CTG ACT CCA AAT ATC ATC TG3' (SEQ. ID. NO. 9) and 5'GAG AAG CAT CTA CAC AAG TC3' (SEQ. ID. NO. 10). Amplification with this set of primers resulted in a 367 bp PCR product containing a Fok I restriction site.

Genotypes for each of the five polymorphisms were evaluated against the three dependent variables provided in Table 2, with diagnoses based on the criteria of the Third Revised Diagnostic and Statistical Manual (DSM-III-R) of the American Psychiatric Association (1987). The differences across the two or three genotypes available at each locus were evaluated either by ANOVA or Student's t-test for continuous variables, and chi-square ($X^2$) with Yates' correction for categorical data.

The 41 males selected for low and high LR were similar in age (about 39 years), marital status (about 73% married), and education (only 5% lacked a college education). Consistent with prior reports (Schuckit and Smith 1996), the low LR subjects were significantly more likely to have been diagnosed as alcohol dependent during the 15-year follow-up (64.7% vs. 8.3%, $\chi^2=14.6$, df=1, p<0.002). There were no significant differences in the self-reported ethnic group of origin ($\chi^2=7.16$, df=5, p=0.21), and all subjects were Caucasian.

Table 2 presents the genotype by trait analyses for each candidate gene locus. For the 5-HTT polymorphism, significantly lower LR scores were observed at age 20 for the 14 subjects with the LL genotype (p=0.04). Consistent with these observations, subjects with the LL genotype were significantly more likely to have fulfilled criteria for alcohol abuse or dependence at some time during the 15 years of follow-up (p=0.04), but there were no differences across groups in the proportion with alcoholic relatives. Because of evidence that the 5-HTT S allele might act in a dominant fashion (Heils et al *J Neurochem* 66:2621–2624 (1996)), the combined SL and SS genotype groups were compared to the LL group, with results supporting an enhanced and statistically significant difference on the mean LR (−0.89±1.00 vs 0.16±0.75, t=2.64, df=39, p=0.01), and on the proportion with an alcoholic diagnosis (57.1% vs 18.5%, $X^2=6.35$, df=1, p=0.02). While not shown in the Table due to overlap with the mean LR score, we have also evaluated the proportion of subjects whose LR fell into the lowest third for comparability to prior publications. This proportion was also significantly higher for the LL group (71.4% LL, 31.6% SL, and 12.5% SS; $X^2=8.7$, df=2, p=0.02).

TABLE 2

The Relationship of 5 Candidate Gene Polymorphisms to LR, Alcoholism Diagnosis, and Family History of Alcoholism

| | 5-HT Transporter | | | | 5-HT$_{2A\,T102C}$ | | | | 5-HT$_{2A\,TYR}$ | | |
|---|---|---|---|---|---|---|---|---|---|---|---|
| | LL | SL | SS | | TT | TC | CC | | His-His | His-Tyr | |
| n = | 14 | 19 | 8 | stat | 6 | 14$^x$ | 19 | stat | 36 | 5 | stat |
| x̄(±SD)LR | −.89 (1.00) | −.30 (.85) | −.00 (.45) | F = 3.63 p = .04 | −.71 (1.04) | −.31 (1.04) | −.46 (.75) | F = .42 p = .66 | −.44 (.94) | −.20 (.70) | t = .57 p = .58 |
| % Alcohol Dx | 57.1 | 21.1 | 12.5 | $\chi^2$ = 6.54 p = .04 | 16.7 | 50.3 | 26.3 | $\chi^2$ = 2.92 p = .24 | 33.3 | 20.0 | $\chi^2$ = .36 p = .55 |
| % FHP | 71.4 | 73.7 | 62.5 | $\chi^2$ = .35 p = .84 | 50.0 | 71.4 | 78.9 | $\chi^2$ = 1.89 p = .39 | 72.2 | 60.0 | $\chi^2$ = .32 p = .57 |

| | | 5-HT$_{2C\,CYS\_SER}$ | | | GABA$_{A\alpha6}$ | | |
|---|---|---|---|---|---|---|---|
| | | Cys | Ser | | Pro/Pro | Pro/Ser | |
| n = | | 38 | 3 | stat | 34 | 7 | stat |
| x̄(±SD)LR | | −.39 (.90) | −.73 (1.13) | t = .63 p = .54 | −.27 (.92) | −1.01 (.80) | t = 1.99 p = .06 |
| % Alcohol Dx | | 31.6 | 33.3 | $\chi^2$ = .004 p = .95 | 23.5 | 71.4 | $\chi^2$ = 6.15 p = .02 |
| FHP | | 71.1 | 66.7 | $\chi^2$ = .03 p = .87 | 64.7 | 100 | $\chi^2$ = 3.49 p = .07 | x The analyses were not available for 2 subjects.

Associations of the GABA$_{A\alpha6}$ genotype to both LR and alcoholism were also observed. Here, Pro/Ser heterozygous individuals were more likely than Pro385 homozygotes to be alcoholic (p=0.02), and they also demonstrated fronds for a lower LR score (p=0.06) and a higher proportion of FHPs (p=0.07). While not shown in Table 2, those with Ser385 were more likely to be in the lowest third in response to alcohol (71.4% vs. 35.3%, $X^2=3.12$, df=1, p=0.08). Comparisons across the genotypes for the 5-HT$_{T102C}$, 5-HT$_{2Atyr}$ His452tyr, and the 5-HT$_{2c}$ Cys23Ser polymorphisms demonstrated no relationship of genotypes to either LR scores or alcoholism diagnoses.

An analysis was also carried out combining information regarding the 5-HTT and GABA$_{A\alpha6}$ polymorphisms. The four men with a combination of both LL 5-HTT and Ser385 GABA$_A$ α6 genotypes (the two associated most closely with low LR and alcoholism) had the lowest LR at age 20 (−1.29±0.53 vs. −0.74±1.13 for LL/PP, 0.59±1.11 for SL/PS, −0.13±0.88 for SL/PP and 0.03±0.45 for SS/PP—test for linear trend t=2.86, df=4, p<0.007). All four of these subjects fell into the lowest third of LR, all were alcoholic, and all were FHP. At the other extreme, the eight men carrying both the SS 5-HTT and the Pro385 GABA$_A$ receptor genotypes (the two genotypes associated with the highest LR scores and nonalcoholic status) had the highest overall LR score, and were the least likely to be alcoholic. There was no evidence of an interaction between the 5-HTT and GABA$_{A\alpha6}$ genotypes (F(1,36)=0.01, p=0.92). As was true in the single locus analysis, these two-locus results reach even higher levels of statistical significance if all subjects with at least one copy of the dominant S allele are combined into one group.

The analysis above demonstrates the significant relationship to LR and alcoholism at two loci, the 5-HTTLPR serotonin transporter variant and the GABA$_A$ α6 amino acid substitution Ser385. Evidence supporting the importance of the GABA$_A$ receptor system in the effects of alcohol and the development of alcoholism is scant. The results above verify that the Pro385Ser polymorphism is indicative of LR and future alcoholism. Furthermore, the disclosure above clearly indicates that genotyping of the human α6 subunit of the GABA$_A$ receptor gene is useful for predicting whether an individual will exhibit a particular sensitivity to ethanol and/or benzodiazepine drugs.

The Existence of More Polymorphisms Associated with BZD and Ethanol Insensitivity Those having ordinary skill in the art will appreciate that direct gene analysis using the SSCP technique may not be sufficiently sensitive to detect all possible sequence variants of the GABA$_A$ α6 receptor gene. In view of the fact that 40% of the GABA$_A$ α6 receptor gene coding sequence was not screened in this study, it is possible that unknown variants in either the coding sequence or promoter region of the α6 gene are in linkage disequilibrium with the Pro385Ser and G1031C variants described herein. In light of the findings presented above and the disclosure which follows, the discovery of more GABA$_A$ α6 receptor polymorphisms that are associated with ethanol and Benzodiazepine drug sensitivty would be routine. Regardless of the particular polymorphism used as a marker of genetically determined sensitivity to ethanol and benzodiazepine drugs, our findings indicate that methods based on α6 genotyping in humans can determine a predisposition to benzodiazepine/ethanol sensitivity. The section below describes many approaches that can be used to identify more polymorphisms in the GABA$_A$ α6 receptor gene that lead to BZD and ethanol insensitivity.

Characterization of Pro385Ser by Computational Analysis

Preliminary computational analysis revealed that the Pro385Ser polymorphism occurs in the second intracellular domain of the receptor near a putative protein kinase C phosphorylation site. Homology searches of nucleic acid and protein databases using software known to those of skill in the art can reveal other transmembrane proteins with a similar motif and can provide a greater understanding of how the Pro385Ser polymorphism confers BZD/ethanol insensitivity. Furthermore, by employing conventional approaches in protein modeling and methods of rational drug design, models of the three-dimensional structure of Pro385 or Ser385 GABA$_A$ α6 can be obtained and agents that interact or circumvent Pro385 or Ser385 GABA$_A$ α6 can be identified. Examples 3–6 disclose several software and hardware embodiments and provide computational methods that can be used to further characterize the Pro385 or Ser385 GABA$_A$ α6 nucleic acid and polypeptide sequences and develop drugs that interact with the Pro385 or Ser385 GABA$_A$ α6 receptors.

Aspects of the invention also include recombinant vectors, probes, and primers comprising Pro385 or Ser385 GABA$_A$ α6 sequence. The discussion below describes embodiments having Pro385 or Ser385 GABA$_A$ α6 nucleic acids.

Use of Nucleic Acids Encoding Pro385 or Ser385 GABA$_A$ α6, or Portions Thereof

The sequence of the Pro385 and Ser385 GABA$_A$ α6 is provided in the sequence listing (SEQ. ID NOs. 11 and 12). Wild-type and/or mutant Pro385 or Ser385 GABA$_A$ α6 sequences, their functional equivalents, or fragments of these sequences at least six nucleotides in length encoding Pro385 or Ser385 GABA$_A$ α6 can be used in accordance with embodiments of the invention. Preferably, the nucleic acid embodiments comprise at least 12, 15, or 17 consecutive nucleotides from the extended cDNA (or genomic DNAs obtainable therefrom). More preferably, the nucleic acid embodiments comprise at least 20–30 consecutive nucleotides from the extended cDNA (or genomic DNAs obtainable therefrom). In some cases, the nucleic acid embodiments comprise more than 30 nucleotides from the nucleic acids encoding Pro385 or Ser385 GABA$_A$ α6, or portions thereof. In other cases, the nucleic acid embodiments comprise at least 40, at least 50, at least 75, at least 100, at least 150, or at least 200 consecutive nucleotides from the nucleic acids encoding Pro385 or Ser385 GABA$_A$ α6, or portions thereof. The nucleic acids listed in SEQ. ID Nos. 9–10 are desirable embodiments, for example. Subsequences comprising hybridizable portions of Pro385 or Ser385 GABA$_A$ α6 sequence have use, e.g., in nucleotide acid hybridization assays, Southern and Northern Blot analysis, etc., as will be described infra.

Some embodiments comprise recombinant nucleic acids having all or part of the Pro385 or Ser385 GABA$_A$ α6 gene. A recombinant construct can be capable of replicating autonomously in a host cell. Alternatively, the recombinant construct can become integrated into the chromosomal DNA of the host cell. Such a recombinant polynucleotide comprises a polynucleotide of genomic or cDNA, of semi-synthetic or synthetic origin by virtue of human manipulation. Therefore, recombinant nucleic acids comprising sequences otherwise not naturally occurring are provided by embodiments of this invention. Although Pro385 or Ser385 GABA$_A$ α6 as it appears in nature can be employed, it will often be altered, e.g., by deletion, substitution, or insertion and will be accompanied by sequence not present in a human.

The nucleotide acid sequence depicted in the sequence listing (SEQ. ID NO. 12) can be altered by mutation such as substitutions, additions, or deletions that provide for sequences encoding functionally equivalent molecules. According to one embodiment, a molecule is functionally equivalent or active compared with a molecule having the sequence depicted in SEQ. ID NO: 11 or 12 if it has the ability to confer ethanol or BZD insensitivity. Due to the degeneracy of nucleotide coding sequences, other DNA sequences which encode substantially the same amino acid sequence as derived from the sequence listing (SEQ. ID NO: 11 or 12) can be used in some embodiments of the present invention. These include, but are not limited to, nucleic acid sequences comprising all or portions of the Pro385 or Ser385 GABA$_A$ α6 gene which have been altered by the substitution of different codons that encode a functionally equivalent amino acid residue within the sequence, thus producing a silent change.

In addition, recombinant Pro385 or Ser385 GABA$_A$ α6-encoding nucleic acid sequences of the invention can be engineered so as to modify processing or expression of Pro385 or Ser385 GABA$_A$ α6. For example, and not by way of limitation, the Pro385 or Ser385 GABA$_A$ α6 gene can be combined with a promoter sequence and/or ribosome binding site, or a signal sequence can be inserted upstream of Pro385 or Ser385 GABA$_A$ α6 encoding sequences to permit secretion of Pro385 or Ser385 GABA$_A$ α6 and thereby facilitate harvesting or bioavailability. Additionally, a given Pro385 or Ser385 GABA$_A$ α6 nucleic acid can be mutated in vitro or in vivo, to create and/or destroy translation, initiation, and/or termination sequences, or to create variations in coding regions and/or form new restriction sites or destroy preexisting ones, or to facilitate further in vitro modification. Any technique for mutagenesis known in the art can be used, including but not limited to, in vitro site-directed mutagenesis (Hutchinson et al., *J. Biol. Chem.* 253:6551 (1978)).

By using the Pro385 or Ser385 GABA$_A$ α6 nucleic acid sequences disclosed in the sequence listing (SEQ ID NO. 12), probes can be designed and manufactured by oligonucleotide synthesis and cDNA or genomic libraries can be screened so as to isolate natural sources of the nucleic acid embodiments and homologs thereof. Alternatively, such nucleic acids can be provided by amplification of sequences resident in genomic DNA or other natural sources by PCR. Example 7 describes the preparation of PCR primers and the amplification of Pro385 or Ser385 GABA$_A$ α6 DNA.

The nucleic acids of the invention can also be used as reagents in isolation procedures and diagnostic assays. For example, sequences from nucleic acids encoding Pro385 or Ser385 GABA$_A$ α6, or portions thereof can be detectably labeled and used as probes to isolate other sequences capable of hybridizing to them. In addition, sequences from nucleic acids encoding Pro385 or Ser385 GABA$_A$ α6, or portions thereof can be used to make PCR primers by conventional oligonucleotide synthesis for use in isolation and diagnostic procedures. The discussion that follows describes some of the expression constructs and protein embodiments of the invention.

Pro385 or Ser385 GABA$_A$ α6 Peptides and Their Expression

Pro385 or Ser385 GABA$_A$ α6 proteins, or fragments, or derivatives thereof include, but are not limited to, those containing as a primary amino acid sequence all or part of the amino acid sequence substantially as deduced from the sequence listed in SEQ. ID NO: 11 or 12 including altered sequences in which functionally equivalent amino acid residues are substituted for residues within the sequence resulting in a silent change. Accordingly, one or more amino acid residues within the sequence can be substituted by another amino acid of a similar polarity which acts as a functional equivalent, resulting in a silent alteration. Substitutes for an amino acid within the sequence can be selected from other members of the class to which the amino acid belongs. For example, the non-polar (hydrophobic) amino acids include alanine, leucine, isoleucine, valine, proline, phenylalanine, tryptophan, and methionine. The polar neutral amino acids include glycine, serine, threonine, cysteine, tyrosine, asparagine and glutamine. The positively charged (basic) amino acids include arginine, lysine, and histidine. The negatively charged (acidic) amino acids include aspartic acid and glutamic acid. In other aspects of the invention, Pro385 or Ser385 GABA$_A$ α6 proteins or fragments or derivatives thereof, which are differentially modified during or after translation, e.g., by phosphorylation, glycosylation, cross-linking, acylation, proteolytic cleavage, linkage to an antibody molecule, membrane molecule, or other ligand, are contemplated. (Ferguson et al., *Ann. Rev. Biochem.* 57:285–320 (1988)).

In one embodiment, the inventors contemplate Pro385 or Ser385 GABA$_A$ α6 or a portion thereof, in a cell line. Further, the present inventors envision isolating or purifying Pro385 or Ser385 GABA$_A$ α6 protein. Example 8 provides several approaches to synthesize, express, and isolate or purify the Pro385 or Ser385 GABA$_A$ α6 protein, or fragments thereof. The term "isolated" requires that the material be removed from its original environment (e.g., the natural environment if it is naturally occurring). For example, a naturally occurring nucleic acid or protein present in a living cell is not isolated, but the same nucleic acid or protein, separated from some or all of the coexisting materials in the natural system, is isolated. In accordance with this definition, Pro385 or Ser385 GABA$_A$ α6 nucleic acid or protein or Pro385 or Ser385 GABA$_A$ α6 nucleic acid or polypeptide fragments present in a cell lysate are "isolated". The term "purified" does not require absolute purity; rather it is intended as a relative definition. For example, recombinant nucleic acids and proteins are routinely purified to electrophoretic homogeneity, as detected by ethidum bromide staining or Coomassie staining, and are suitable in several assays despite having the presence of contaminants. Example 8 provides several approaches to synthesize, express, and isolate or purify the Pro385 or Ser385 GABA$_A$ α6 protein, or fragments thereof. Following synthesis or expression and purification of the proteins encoded by the Pro385 or Ser385 GABA$_A$ α6 nucleic acid or portion therof, the purified proteins can be used to generate antibodies as described in the following section.

Production of an Antibody to a Pro385 or Ser385 GABA$_A$ α6 Polypeptide

The antibodies contemplated have many uses including, but not limited to, biotechnological applications, therapeutic/prophylactic applications, and diagnostic applications. While antibodies capable of specifically recognizing the protein of interest can be generated using synthetic 15-mer peptides having a sequence encoded by Pro385 or Ser385 GABA$_A$ α6 gene or portion thereof by injecting the synthetic peptides into mice to generate antibody, a more diverse set of antibodies can be generated using recombinant or purified Pro385 or Ser385 GABA$_A$ α6 protein or fragments thereof, as described in Example 9. The discussion that follows describes several diagnostic embodiments of the invention.

Diagnostic Embodiments

Generally, the diagnostics and methods of use thereof can be classified according to whether the diagnostic detects the presence of Pro385 or Ser385 GABA$_A$ α6 nucleic acid in a sample or Pro385 or Ser385 GABA$_A$ α6 protein in a sample. Accordingly, the detection of the Pro385 or Ser385 GABA$_A$ α6 nucleic acid and/or protein in a biological sample indicates a predilection to BZD/ethanol insensitivity. Additionally, the manufacture of kits which incorporate the reagents and methods described in the following embodiments so as to allow for the rapid detection of the Pro385Ser polymorphism are contemplated. The diagnostic kits can include a nucleic acid probe or an antibody that specifically detects the Pro385Ser polymorphism, for example, or can detect both wild-type and mutant. The detection component will typically be supplied in combination with one or more of the following reagents. A substratum capable of absorbing or otherwise binding DNA, RNA, or protein will often be supplied. Available substrata for this purpose includes membranes of nitrocellulose, nylon or derivatized nylon that can be characterized by bearing an array of positively charged substituents. One or more restriction enzymes, such as FokI, can be furnished in the kit, as can non-human polynucleotides like calf-thymus or salmon-sperm DNA.

Useful nucleic acid-based diagnostic techniques include, but are not limited to, fluorescent in situ hybridization (FISH), direct DNA sequencing, PFGE analysis, Southern Blot analysis, single-stranded confirmation analysis (SSCA), RNase protection assay, dot blot analysis, and PCR. The starting point for these analysis is isolated or purified DNA from a biological sample. Most simply, blood is drawn from the subject to be tested and DNA extracted from the nucleated cells in the blood. In some cases, primers corresponding to regions of Pro385Ser can be used with PCR to amplify this DNA so that it can be more easily be detected in diagnostic applications.

Several methods can be used to detect the Pro385Ser polymorphism in a biological sample. Direct DNA sequencing, either manual sequencing or automated fluorescent sequencing can detect sequence variation. Another approach is the single-stranded confirmation polymorphism assay (SSCA) (Orita et al., *Proc. Natl. Acad. Sci. USA* 86:2776–2770 (1989)) discussed above. This method, however, does not detect all sequence changes, especially if the DNA fragment size is greater than 200 base pairs, but can be optimized to detect most DNA sequence variation. The reduced detection sensitivity is a disadvantage, but the increased throughput possible with SSCA makes it an attractive, viable alternative to direct sequencing for mutation detection. The fragments which have shifted mobility on SSCA gels are then sequenced to determine the exact nature of the DNA sequence variation. Other approaches based on the detection of mismatches between the two complimentary DNA strands include clamped denaturing gel electrophoresis (CDGE) (Sheffield et al., *Am. J. Hum. Genet.* 49:699–706 (1991)), heteroduplex analysis (HA) (White et al., *Genomics* 12:301–306 (1992)), and chemical mismatch cleavage (CMC) (Grompe et al., *Proc. Natl. Acad. Sci. USA* 86:5855–5892 (1989)). A review of currently available methods of detecting DNA sequence variation can be found in a recent review by Grompe, *Nature Genetics* 5:111–117 (1993).

A rapid preliminary analysis to detect polymorphisms and DNA sequences can be performed by looking at a series of Southern Blots of DNA cut with one or more restriction enzymes preferably with a large number of restriction enzymes. Each block contains lanes of DNA from uninfected individuals and the DNA to be tested. Southern Blots displaying hybridizing fragments when probed with sequences corresponding to Pro385Ser indicate the presence of the genotype associated with BZD/ethanol insensitivity. Detection of point mutations can also be accomplished by amplifying the DNA directly from the sample using primers corresponding to the regions of Pro385Ser by standard PCR techniques. The DNA sequence of the amplified sequences can then be determined.

There are six well-known methods for confirming the presence of Pro385Ser: 1) single-stranded confirmation analysis (SSCA) (Orita et al.); 2) denaturing gradient gel electrophoresis (DGGE) (Wartell et al., *Nucl. Acids Res.* 18:2699–2705 (1990), Sheffield et al., *Proc. Natl. Acad. Sci. USA* 86:232–236 (1989), 3) RNase protection assays (Finkelstein et al., *Genomics* 7:167–172 (1990), Kinszler et al., *Science* 251:1366–1370 (1991)); 4) the use of proteins which recognize nucleotide mismatches, such as the *E. Coli* mutS protein (Modrich, *Ann. Rev. Genet.* 25:229–253 (1991); and allele-specific PCR (Rano and Kidd, *Nucl. Acids Res.* 17:8392 (1989)). For allele-specific PCR, primers are used which hybridize at their 3' ends to the Ser385 GABA$_A$ α6 mutation. If the particular Ser385 mutation is not present, an amplification product is not observed. Amplification Refractory Mutation System (ARMS) can also be used, as disclosed in European Patent Application Publication No. 0332435 and in Newton et al., *Nucl. Acids Res.* 17:2503–2516 (1989).

In the first methods (SSCA, DGGE, and RNase protection assay), a new electrophoretic band appears. SSCA detects a band which migrates differentially because the sequence change causes a difference in single-strand, intramolecular base pairing. RNase protection involves cleavage of the mutant polynucleotide into two or more smaller fragments. DGGE detects differences in migration rates of sequences compared to wild-type sequences, using a denaturing gradient gel. In an allele-specific oligonucleotide assay (ASOs) (Conner et al., *Proc. Natl. Acad. Sci. USA* 80:278–282 (1983)), oligonucleotide is designed which detects a specific sequence, and an assay is performed by detecting the presence or absence of hybridization signal. In the mutS assay, the protein binds only to sequences that contain a nucleotide mismatch in a heteroduplex between mutant and wild-type sequences.

Mismatches, according the present invention, are hybridized nucleic acid duplexes in which the two strands are not 100% complementary. Lack of total homology can be due to deletions, insertions, inversions, or substitutions. Mismatched detection can be used to detect point mutations in the gene or in its mRNA product. While these techniques are less sensitive than sequencing, they are simpler to perform on a large number of biological samples.

An example of a mismatch cleavage technique is the RNase protection method. In practice, the method involves the use of a labeled riboprobe which is complementary to the Ser385 gene coding sequence. The riboprobe and either mRNA or DNA isolated from the biological sample are annealed (hybridized) together and subsequently digested with the enzyme RNase A which is able to detect some mismatches in a duplex RNase structure. If a mismatch is detected by RNase A, it cleaves at the site of the mismatch. Thus, when the annealed RNA is separated on a electrophoretic gel matrix, if a mismatch has been detected and cleaved by RNase A, an RNA product will be seen which is much smaller than the full length duplex RNA for the riboprobe and the mRNA or DNA. The riboprobe need not be the fall length of Pro385 or Ser385 GABA$_A$ α6 mRNA or gene, it will be desirable to use a number of these probes to screen the whole mRNA sequence for mismatches. In a similar fashion, DNA probes can be used to detect mismatches, through enzymatic or chemical cleavage. See, e.g., Cotton, et al., *Proc. Natl. Acad. Sci. USA* 85:4397 (1988), Shenk et al., *Proc. Natl. Acad. Sci. USA* 72:989 (1975), Novack et al., *Proc. Natl. Acad. Sci. USA* 83:586 (1986).

Alternatively, mismatches can be detected by shifts in the electrophoretic ability of mismatched duplexes relative to matched duplexes. (See, e.g., Cariello, *Human Genetics* 42:726 (1988)). With either riboprobes or DNA probes, the cellular mRNA or DNA which might contain the Ser385 gene can be amplified by PCR before hybridization. DNA sequences isolated from biological samples which have been amplified by use of PCR can be screened using allele-specific probes. These probes are nucleic acid oligomers, each of which contains a region of Ser385 sequence. For example, one oligomer can be about 30 nucleotides in length and corresponds to a portion of the Ser385 sequence referenced in SEQ ID NO. 12 By use of a battery of such allele-specific probes, PCR amplification products can be screened to identify the presence of the Pro385Ser polymorphism. Hybridization of allele-specific probes with amplified Pro385 or Ser385 GABA$_A$ α6 sequences can be performed, for example, on a nylon filter.

The most definitive test for the presence of the Pro385Ser polymorphism, is to directly compare nucleotide or protein sequences isolated from a biological sample with those from a control population. The control population, for example, can contain DNA, RNA, cDNA nucleic acids samples representative of the wild-type sequence, as listed in SEQ ID NO. 11 (experimental being the Pro385Ser polymorphism, as listed in SEQ ID NO. 12) Alternatively, one could sequence messenger RNA after amplification, e.g., by PCR. Examples 10–13 describe nucleic acid-based diagnostic methods of the invention.

In addition to the diagnostics and methods based on the detection of nucleic acid that encodes to Pro385 or Ser385 GABA$_A$ α6, diagnostics and methods based on the detection of Pro385 or Ser385 GABA$_A$ α6 proteins are also envisioned. The following discussion details several embodiments of this aspect of the invention.

Protein-Based Diagnostic Embodiments

The presence of Pro385 or Ser385 GABA$_A$ α6 protein can be detected by screening for the presence of the protein using conventional assays. For example, monoclonal antibodies immunoreactive with Pro385 GABA$_A$ α6 protein can be used to screen biological samples for the presence of the Pro385Ser polymorphism. Similarly, antibodies specific for or Ser385 GABA$_A$ α6 protein can be used to screen for the presence of the Pro385Ser polymorphism. Such immunological assays can be done in many convenient formats.

In a preferred embodiment, antibodies will immunoprecipitate specifically the Ser385 GABA$_A$ α6 protein (e.g., will not cross-react with the Pro385 protein) from solution as well as react specifically with Ser385 protein on Western or Immunoblots of polyacrylamide gel. In another preferred embodiment, antibodies will detect Ser385 in paraffin or frozen sections, using immunocytochemical techniques. Preferred embodiments relating to methods for detecting the Pro385 or Ser385 GABA$_A$ α6 protein include enzyme-linked immunosorbant assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al., in U.S. Pat. Nos. 4,376,110 and 4,486,530, hereby incorporated by reference.

We also contemplate the preparation of diagnostic kits comprising antibodies specific for the Ser385 protein and not cross-reactive with the Pro385 protein. Such kits can also include nitrocellulose or nylon membranes for immobilizing protein from a biological sample to be tested. Results from the kit assays can be interpreted by a healthcare provider or a diagnostic laboratory. Alternatively, diagnostic kits are manufactured and sold to private individuals for self-diagnosis. In addition, we contemplate the design and manufacture of supports having Pro385 or Ser385 GABA$_A$ α6 polypeptides, as described below, for use in methods for identifying agents that interact with the Pro385 or Ser385 GABA$_A$ α6 polypeptides.

Construction of a Multimeric Support Having Pro385 or Ser385 GABA$_A$ α6 or Polypeptide Fragments Thereof A biotechnological tool that is useful for the discovery of agents that interact with Pro385 or Ser385 GABA$_A$ α6 or circumvent Pro385 or Ser385 GABA$_A$ α6 (e.g., high throughput screening) desirably provide Pro385 or Ser385 GABA$_A$ α6 in such a form or in such a way that a sufficient affinity for the agent is obtained. For example, while monomeric Pro385 or Ser385 GABA$_A$ α6 (i.e. appearing as a discrete unit of the protein on a support) is sufficiently active to mediate association with an agent, multimeric Pro385 or Ser385 GABA$_A$ α6 (i.e. appearing as multiple units of the protein on a support) can have a far greater affinity for the agent and would provide sufficient binding events to be detectable by conventional methods. Example 14 provides several approaches that can be used to create a multimeric support having Pro385 or Ser385 GABA$_A$ α6 or polypeptide fragments thereof. The multimeric supports can be used in methods of high throughput screening, several of which are described in the following section.

High Throughput Screening for Agents That Interact With Pro385 or Ser385 GABA$_A$ α6 Protein, or Polypeptide Fragments Thereof High throughput screening is an approach to drug discovery that searches for a protein, peptide, peptidomimetic, or chemical that will interact on a defined target such as the Pro385 or Ser385 GABA$_A$ α6 protein, or a polypeptide fragment thereof. Generally, a library of proteins, polypeptides, peptides, peptidomimetics, or chemicals, collectively referred to as "agents", is screened against the target in biological assays and agents which interact with the target are identified and used directly as therapeutics or as a basis to develop new therapeutics using combinatorial chemistry and protein modeling. Example 15 provides several high throughput screening methods that are used to identify agents that interact with Pro385 or Ser385 GABA$_A$ α6 protein or polypeptide fragments thereof.

Example 1 describes the methods that were used to measure BZD sensitivity in human subjects.

EXAMPLE 1

COAs were tested on two days about one week apart. Intravenous catheters were inserted into antecubital veins in each of the subjects arms. One intravenous line was used for drawing blood while the other was used for administration of either diazepam or placebo. Infusions were given in a double blind fashion and in randomized order. On the day that diazepam was administered, the drug was delivered at 15-minute intervals in four doses of 25, 25, 50, and 100 μg/kg (yielding logarithmically increasing cumulative doses of 25, 50, 100, and 200 μg/kg). Each dose was injected over the course of 60 seconds. On the day that the placebo was administered, saline was injected in similar volumes and at the same times.

On each testing day, responses were measured at 12 separate time points: twice at baseline, once after each of the four doses, and at each of six 30 minute intervals after the last dose for a period spanning three hours. Eye movements were evaluated at each time point. Blood was drawn for plasma diazepam levels at each time point from the arm contralateral to that used for drug injection. Plasma diazepam concentrations were measured by electron-capture gas-liquid chromatography according to the method described by Greenblatt et al., in *Psychopharmacology* 70:89 (1980). Levels of the primary diazepam metabolite, desmethyldiazepam, were also quantitated, but in all cases desmethyldiazepam levels were much lower than levels of the parent drug.

Peak saccadic eye movement velocity and average smooth pursuit eye movement gain were recorded as described by Cowley et al., in *Alcohol Clin Exp Res* 18:324 (1994) using a non-invasive infrared oculographic device (Eye Trac model 210, ASL Laboratories, Waltham, Mass.) with a precision of ±0.25 degrees. In the saccadic eye movement task subjects followed a series of 27 flashing targets, each presented for 2 seconds. Target steps varied randomly from 3 to 27 degrees in amplitude. Since saccadic velocity increases in a curvilinear fashion as a function of amplitude (a relationship known as the "main sequence"), the velocities at various amplitudes were fitted to an exponential equation of the form: peak velocity=a−b$^{-x/c}$ where x=saccade amplitude and a, b, and c are constants. (Bahill et al., *Math Biosci* 24:191 (1975)). The main sequence was used to calculate the peak velocity for an idealized 20 degree saccade at each time point for each subject.

During the smooth pursuit task, the target moved in a trapezoidal pattern, between 15 degrees to the left and 15 degrees to the right of center, at a constant velocity of 10 degrees per second. After two practice ramps, data were collected from 14 ramps, each 3 seconds in duration. After identification of saccades and artifacts, remaining pursuit segments were used to compute time-weighted average gain (eye velocity/target velocity as described by Abel et al., in *Biol Psychiatry* 29:1063 (1991)). Example 2 describes methods that were used to identify genetic polymorphisms in the polynucleotide sequences encoding the GABA$_A$ α6 subunit.

EXAMPLE 2

Amplification of genomic DNA isolated from Epstein-Bar immortalized lymphoblastoid cell lines was carried out using the five primer palm listed in Table 3. These primer pairs amplified five non-overlapping regions covering 60.3% of the human GABA$_A$ α6 receptor gene coding sequence. (Hadingham et al., *Mol Pharmacol* 49:253 (1996)). Since the polynucleotide sequences of the human GABA$_A$ α6 receptor introns were unknown, all primers were designed to be complementary to exon sequences adjacent to the exon-intron boundaries. Positions of the boundaries were predicted based on the sequence encoding the mouse α6 subunit (Jones et al., *J Neurochem* 67:907 (1996)). Identity of the amplification products was confirmed by DNA sequencing. The amplification product from the GABA$_A$ α6-1f and GABA$_A$ α6-2b primer pair included 202 bp of the first intron. The polynucleotide sequence of this intron segment was deposited with GenBank and assigned accession number AF053072 and provides one useful region from which primers can be designed. One of skill in the art, however, will appreciate that many primers which span the Pro385Ser polymorphism can be designed.

DNA amplification was performed by Polymerase Chain Reaction (PCR) using a GENEAMP PCR System 9600 (Perkin-Elmer, Norwalk, Conn.) with the following conditions: 95° C. for 3 minutes; 30 cycles of: 94° C. for 15 seconds; 60° C. for 20 seconds; 72° C. for 30 seconds; followed by 72° C. for 10 minutes. The reaction mixture was in a 5 μl volume containing 50 ng sample DNA, 50 nM of each primer, 50 μM each DNTP, 1× Perkin Elmer buffer I, and 0.125 units of Taq DNA polymerase. 0.033 μl [α-$^{32}$P] dCTP (3,000 Ci/mmol) was included in the PCR reaction. At the conclusion of the amplification reaction, a solution containing 95% formamide, 10 mM NaOH, 0.05% xylene cyanol and 0.05% bromphenol blue was added to each sample to give a total volume of 50 μl.

Sequence variants were initially detected using the single strand conformational polymorphism (SSCP) method described by Orita et al., in *Proc Natl Acad Sci USA* 86:2766 (1989). After denaturing the DNA at 80° C. for 5 minutes, 1 μl of the mixture was loaded on an MDE™ Gel (FMC BioProducts, Rockland, Me.) and separated by electrophoresis at 4° C. at 9 Watts. Following electrophoresis, the gel was dried and exposed to Kodak XAR film for 0.5–8 hours at room temperature to visualize the positions of radiolabeled polynucleotides.

TABLE 3

Primers for Amplifying the GABA$_A$ α6 Receptor Coding Sequence

| Primer | Primer Sequence | Nucleotide position (5'–3') | PCR product (bp) |
|---|---|---|---|
| GABA$_A$α6-1f | 5' ATGGCGTCATCTCTGCCCTG 3' (SEQ ID NO:1) | 1 to 20 | 359 (202 bp intron) |
| GABA$_A$α6-2b | 5' CTCCAAATCCCGGCCGCAGC 3' (SEQ ID NO:2) | 138 to 157 | |
| GABA$_A$α6-4f | 5' GGACTGATGAGAGGTTGAAG 3' (SEQ ID NO:3) | 260 to 279 | 185 |
| GABA$_A$α6-4b | 5' CATGGTGTATAAAATGGTTC 3' (SEQ ID NO:4) | 444 to 425 | |
| GABA$_A$α6-7f | 5' GTGAATACGTTATAATGACA 3' (SEQ ID NO:5) | 674 to 693 | 153 |
| GABA$_A$α6-7b | 5' CAAAAACAGTTCTTGCTG 3' (SEQ ID NO:6) | 826 to 809 | |
| GABA$_A$α6-8f | 5' GGATCACCACTGTTTTAACT 3' (SEQ ID NO:7) | 827 to 846 | 233 |
| GABA$_A$α6-8b | 5' AGTAGCTTTGATATTGTCA 3' (SEQ ID NO:8) | 1059 to 1040 | |
| GABA$_A$α6-9f | 5' CTGACTCCAAATATCATCTG 3' (SEQ ID NO:9) | 1091 to 1110 | 365 |
| GABA$_A$α6-9b | 5' GAGAAGCATCTACACAAGTC 3' (SEQ ID NO:10) | 1436 to 1455 | |

DNA bands showing altered mobility compared to a wild-type control in the SSCP assay were cut out from the gel, immersed in 20 μl of water and then heated 80° C. for 5 minutes. A 1 μl sample of the water-extracted polynucleotide was subjected to direct sequencing (Suzuki et al., *Anal Biochem* 192:82 (1991)) using an ABI PRISM™ dye terminator cycle sequencing kit with a 373 DNA sequencing system (Perkin-Elmer).

Table 4 presents the primer sequences and restriction enzymes used for PCR-RFLP assays that were used for rapid genotyping of the two GABA$_A$ α6 polymorphisms in 56 children of alcoholics. PCR Conditions were the same as those use in the SSCP assay except that the reaction mixture had a volume of 10 μl, contained 100 ng of DNA, 250 nM of each primer, 200 μM each of dNTP and 0.25 units of Taq DNA polymerase. As indicated in Table 4, Fok I and Hae III restriction enzymes were used for detecting the Pro385Ser and G1031C polymorphisms, respectively. Restriction endonuclease digestions were performed using 10 units of the restriction enzyme in a total volume of 20 μl for 2 hours at 37° C. using buffer conditions appropriate for each enzyme. DNA fragments were resolved by electrophoresis on a 5% polyacrylamide gel.

Embodiments of the invention include systems, particularly computer-based systems that contain the sequence information described herein. As used herein, "a computer-based system" refers to the hardware, software, and database used to analyze the Pro385 or Ser385 $GABA_A$ α6 nucleotide sequence and the Pro385 or Ser385 $GABA_A$ α6 protein sequence, or fragments thereof. The computer-based system preferably includes the storage media described above, and a processor for accessing and manipulating the sequence data. The hardware of the computer-based systems of this embodiment comprise a central processing unit (CPU) and

TABLE 4

Two Polymorphisms in the α6 Coding Sequence

| Name of polymorphism | SSCP and RFLP Primers | Nucleotide position | Substitution | RFLP Enzyme | Alleles | Fragment sizes (bp) | Allele frequency |
|---|---|---|---|---|---|---|---|
| G1031C | $GABA_A$α6-8f $GABA_A$α6-8b | +1031 | (GC<u>G</u>-GC<u>C</u>) | Hae III | 1031G 1031C | 233 177 + 56 | 0.53 0.47 |
| Pro385Ser | $GABA_A$α6-9f $GABA_A$α6-9b | +1236 | Pro-Ser (<u>C</u>CC-<u>T</u>CC) | Fok I | Pro385 Pro385Ser | 365 261 + 104 | 0.92 0.08 |

Example 3 describes several computer related embodiments that can be used to identify more polymorphisms in the $GABA_A$ α6 sequence and molecules that interact with the Pro385 or Ser385 $GABA_A$ α6 sequence.

EXAMPLE 3

The Pro385 or Ser385 $GABA_A$ α6 sequence was entered onto a computer readable medium for recording and manipulation. It will be appreciated by those skilled in the art that a computer readable medium having the Pro385 or Ser385 $GABA_A$ α6 sequence is useful for the determination of homologous sequences, structural and functional domains, and the construction of protein models for rational drug design. The functionality of a computer readable medium having the Pro385 or Ser385 $GABA_A$ α6 sequence, for example, includes the ability to compare the sequence, using computer programs known in the art, so as to perform homology searches to identify similar ion transporters, and to develop protein models and conduct rational drug design.

The Pro385 or Ser385 $GABA_A$ α6 sequence can be stored, recorded, and manipulated on any medium which can be read and accessed by a computer. As used herein, the words "recorded" and "stored" refer to a process for storing information on computer readable medium. A skilled artisan can readily adopt any of the presently known methods for recording information on computer readable medium to generate manufactures comprising the nucleotide or polypeptide sequence information of this embodiment of the present invention.

A variety of data storage structures are available to a skilled artisan for creating a computer readable medium having recorded thereon a nucleotide or polypeptide sequence. The choice of the data storage structure will generally be based on the component chosen to access the stored information. Computer readable media include magnetically readable media, optically readable media, or electronically readable media. For example, the computer readable media can be a hard disc, a floppy disc, a magnetic tape, CD-ROM, RAM, or ROM as well as other types of other media known to those skilled in the art. The computer readable media on which the sequence information is stored can be in a personal computer, a network, a server or other computer systems known to those skilled in the art.

one or more databases. A skilled artisan can readily appreciate that any one of the currently available computer-based systems are suitable.

In one particular embodiment, the computer system includes a processor connected to a bus which is connected to a main memory (preferably implemented as RAM) and a variety of secondary storage devices, such as a hard drive and removable medium storage device. The removable medium storage device can represent, for example, a floppy disk drive, a compact disk drive, a magnetic tape drive, etc. A removable storage medium, such as a floppy disk, a compact disk, a magnetic tape, etc. containing control logic and/or data recorded therein (e.g., the Pro385 or Ser385 $GABA_A$ α6 nucleotide sequence or the Pro385 or Ser385 $GABA_A$ α6 polypeptide sequence) can be inserted into the removable storage device. The computer system includes appropriate software for reading the control logic and/or the data from the removable medium storage device once inserted in the removable medium storage device.

The Pro385 or Ser385 $GABA_A$ α6 nucleotide sequence or the Pro385 or Ser385 $GABA_A$ α6 polypeptide sequence can be stored in a well known manner in the main memory, any of the secondary storage devices, and/or a removable storage medium. Software for accessing and processing the Pro385 or Ser385 $GABA_A$ α6 nucleotide sequence or the Pro385 or Ser385 $GABA_A$ α6 polypeptide sequence (such as search tools, compare tools, and modeling tools etc.) reside in main memory during execution.

As used herein, "a database" refers to memory which can store nucleotide or polypeptide sequence information, protein model information, and information on other peptides, chemicals, peptidomimetics, and other agents which interact with proteins. Additionally, a "database" refers to a memory access component which can access manufactures having recorded thereon nucleotide or polypeptide sequence information, protein model information and information on other peptides, chemicals, peptidomimetics, and other agents which interact with proteins. Many databases are known to those of skill in the art and several will be discussed below.

The Pro385 or Ser385 $GABA_A$ α6 sequence data can be stored and manipulated in a variety of data processor programs in a variety of formats. For example, the sequence data can be stored as text in a word processing file, such as MicrosoftWORD or WORDPERFECT or as an ASCII file in a variety of database programs familiar to those of skill in the art, such as DB2, SYBASE, or ORACLE.

A "search program" refers to one or more programs which are implemented on the computer-based system to compare a nucleotide or polypeptide sequence with other nucleotide or polypeptide sequences and compounds including but not limited to peptides, peptidomimetics, and chemicals stored within the database. A search program also refers to one or more programs that compare one or more protein models to several protein models which exist in a database and one or more protein models to several peptides, peptidomimetics, and chemicals that exist in a database. A search program is used, for example, to compare regions of the Pro385 or Ser385 $GABA_A$ α6 gene or the Pro385 or Ser385 $GABA_A$ α6 protein that match sequences in nucleic acid and protein data bases so as to identify homologies and structural or functional motifs. A "retrieval program" refers to one or more programs that are implemented on the computer based system to identify a homologous nucleic acid sequence, a homologous protein sequence, or a homologous protein model. Further, a retrieval program is also used to identify peptides, peptidomimetics and chemicals which interact with a nucleic acid sequence, protein sequence, or protein model.

By one approach, percent sequence identity can be determined by standard methods that are commonly used to compare the similarity and position of the amino acid of two polypeptides. Using a computer program such as BLAST or FASTA, two polypeptides are aligned for optimal matching of their respective amino acids (either along the full length of one or both sequences, or along a predetermined portion of one or both sequences). Such programs provide "default" opening penalty and a "default" gap penalty, and a scoring matrix such as PAM 250 (a standard scoring matrix; see Dayhoff et al., in: Atlas of Protein Sequence and Structure, Vol. 5, Supp. 3 (1978)) can be used in conjunction with the computer program. The percent identity can then be calculated as:

$$\frac{\text{total number of identical matches}}{[\text{length of the longer sequence within the matched span} + \text{number of gaps introduced into the longer sequence in order to align the two sequences}]} \times 100$$

Polypeptides that are at least 70% identical will typically have one or more amino acid substitutions, deletions and/or insertions. Usually, the substitutions will be conservative so as to have little or no effect on the overall net charge, polarity, or hydrophobicity of the protein but optionally can increase the activity of $GABA_A$ α6 receptor. Example 4 provides methods to compare the Pro385 or Ser385 $GABA_A$ α6 gene or the Pro385 or Ser385 $GABA_A$ α6 protein with known databases having nucleotide and protein sequences so as to identify homologies and structural or functional motifs.

EXAMPLE 4

The Pro385 or Ser385 $GABA_A$ α6 gene sequence or the Pro385 or Ser385 $GABA_A$ α6 protein sequence can be compared to known sequences on a nucleotide or protein basis. The Pro385 or Ser385 $GABA_A$ α6 gene sequence or the corresponding full length cDNA can be compared to the following known nucleic acid sequences: vertebrate sequences, EST sequences, patented sequences, and recently identified sequences (Genbank daily releases). The Pro385 or Ser385 $GABA_A$ α6 gene sequence or the corresponding full length cDNA with more than 70% homology over 30 nucleotides using either BLASTN or BLAST2N are identified and matching vertebrate sequences are subsequently examined using FASTA. Ion transporters homologous to Pro385 or Ser385 $GABA_A$ α6, particularly ion transporters having point mutations in transmembrane regions, can be identified in this manner. For example, other members of the $GABA_A$ α ligand activated chloride channel family can be identified by the approach above.

ORFs encoded by sequences of the Pro385 or Ser385 $GABA_A$ α6 gene or the corresponding full length cDNAs are also compared to known amino acid sequences found in Swissprot release 35, PIR release 53 and Genpept release 108 public databases using BLASTP with the parameter W=8 and allowing a maximum of 10 matches. In addition, the three-frame conceptual translation products of the top strand of the Pro385 or Ser385 $GABA_A$ α6 gene sequence or the corresponding full length cDNA are compared to publicly known amino acid sequences of Swissprot using BLASTX with the parameter E=0.001.

Additionally, a search program is used to compare the Pro385 or Ser385 $GABA_A$ α6 with other known sequences so as to generate protein models. Example 5 below describes methods to construct protein models of Pro385 or Ser385 $GABA_A$ α6.

EXAMPLE 5

In the past, the three-dimensional structure of proteins has been determined in a number of ways. Perhaps the best known way of determining protein structure involves the use of x-ray crystallography. A general review of this technique can be found in Van Holde, K. E. Physical Biochemistry, Prentice-Hall, N.J. pp. 221–239 (1971). Using this technique, it is possible to elucidate three-dimensional structure with good precision. Additionally, protein structure can be determined through the use of techniques of neutron diffraction, or by nuclear magnetic resonance (NMR). (See, e.g., Moore, W. J., Physical Chemistry, $4^{th}$ Edition, Prentice-Hall, N.J. (1972)).

Alternatively, the protein model embodiments of the present invention are constructed using computer-based protein modeling techniques. By one approach, the protein folding problem is solved by finding target sequences that are most compatible with profiles representing the structural environments of the residues in known three-dimensional protein structures. (See, e.g., Eisenberg et al., U.S. Pat. No. 5,436,850 issued Jul. 25, 1995). In another technique, the known three-dimensional structures of proteins in a given family are superimposed to define the structurally conserved regions in that family. This protein modeling technique also uses the known three-dimensional structure of a homologous protein to approximate the structure of Pro385 or Ser385 $GABA_A$ α6. (See e.g., Srinivasan, et al., U.S. Pat. No. 5,557,535 issued Sep. 17, 1996). Conventional homology modeling techniques have been used routinely to build models of proteases and antibodies. (Sowdhamini et al., Protein Engineering 10:207, 215 (1997)). Comparative approaches can also be used to develop three-dimensional protein models when the protein of interest has poor sequence identity to template proteins. In some cases, proteins fold into similar three-dimensional structures despite having very weak sequence identities. For example, the three-dimensional structures of a number of helical cytokines fold in similar three-dimensional topology in spite of weak sequence homology.

The recent development of threading methods and "fuzzy" approaches now enables the identification of likely folding patterns and functional protein domains in a number of situations where the structural relatedness between target and template(s) is not detectable at the sequence level. By one method, fold recognition is performed using Multiple Sequence Threading (MST) and structural equivalences are deduced from the threading output using the distance geometry program DRAGON which constructs a low resolution model. A fall-atom representation is then constructed using a molecular modeling package such as QUANTA.

According to this 3-step approach, candidate templates are first identified by using the novel fold recognition algorithm MST, which is capable of performing simultaneous threading of multiple aligned sequences onto one or more 3-D structures. In a second step, the structural equivalences obtained from the MST output are converted into interresidue distance restraints and fed into the distance geometry program DRAGON, together with auxiliary information obtained from secondary structure predictions. The program combines the restraints in an unbiased manner and rapidly generates a large number of low resolution model confirmations. In a third step, these low resolution model confirmations are converted into full-atom models and subjected to energy minimization using the molecular modeling package QUANTA. (See e.g., Aszódi et al., Proteins:Structure, Function, and Genetics, Supplement 1:38–42 (1997)).

Alternatively, the sequence-to-structure-to-function paradigm is exploited by first identifying the structure of a protein from its sequence using a threading algorithm, which aligns the sequences to the best matching structure in a structural database, then identifying the protein's active site from the alignment using a "fuzzy functional form" (FFF), which is a three-dimensional descriptor of the active site of a protein. (See e.g., Fetrow et al., J. Mol. Biol. 282:703–711 (1998) and Fetrow and Skolnick, J. Mol. Biol. 281: 949–968 (1998)). The FFFs are built by itteratively superimposing the protein geometries from a series of functionally related proteins with known structures. The FFFs are not overly specific, however, and the degree to which the descriptors can be relaxed is explored. In essence, conserved and functionally important residues are identifed and a set of geometric and conformational constraints for a specific function are defined in the form of a computer algorithm. The program then searches experimentally determined protein structures from a protein structural database for sets of residues that satisfy the specified constraints.

By using this computational protocol, genome sequence data bases such as maintained by various organizations including: Tigr. University of Wisconsin, Stanford University, U.S. Government, National Institutes of Heath, European Bioinformatics Institute, Pasteur in France, and Massachusetts Institute of Technology can be rapidly screened for specific protein active sites and for identification of the residues at those active sites which resemble Pro385 or Ser385. Several other groups have developed databases of short sequence patterns or motifs designed to identify a given fraction or activity of a protein. These databases, notably prosite blocks and prints use short stretches of sequence information to identify sequence patterns that are specific for a given function; thus they avoid the problems arising from the necessity of matching entire sequences.

Once a protein model of Pro385 or Ser385 has been generated by x-ray crystallography, NMR, neutron diffraction, or computational modeling, methods of rational drug design can be employed so as to elucidate agents which interact or circumvent the Pro385 or Ser385 and, thus, restore BZD/ethanol sensitivity. Standard molecular modeling can be used to compare the structures of the Pro385 or Ser385 proteins and interactive regions with diazepam (and/or homologs or derivatives) and ethanol can be identified and used to discover new therapeutic agents. Also, molecular modeling can be used to design synthetic compounds (e.g., peptides or small molecule organic compounds) that block or interfere with the chloride transport, ligand binding, or ligand mediated modulation or activation of the Pro385 or Ser385 $GABA_A$ α6 protein. Example 6 details several methods of rational drug design.

EXAMPLE 6

In some embodiments, search programs are employed to compare regions of Pro385 or Ser385 gene or the Pro385 or Ser385 protein with molecules having known ligand interactions, such as peptides, peptidomimetics, and chemicals, so that therapeutic interactions of the molecules can be predicted. (Schneider, *Genetic Engineering News* December: page 20 (1998), Tempczyk et al., *Molecular Simulations Inc. Solutions* April (1997), and Butenhof, *Molecular Simulations Inc. Case Notes* (August 1998)). This process is referred to as "rational drug design".

One goal of rational drug design is to produce structural analogs of biologically active polypeptides of interest or of small molecules with which they interact (e.g., agonists, antagonists, inhibitors) in order to fashion drugs that are, for example, more active or stable forms of the polypeptide, or which enhance or interfere with the function of a polypeptide in vivo. (See, e.g., Hodgson, *Bio. Technology* 9:19–21 (1991)). The naturally occurring amino acids employed in the biological production of peptides all have the L-configuration. Synthetic peptides can be prepared employing conventional synthetic methods, utilizing L-amino acids, D-amino acids, or various combinations of amino acids of the two different configurations. Synthetic compounds that mimic the conformation and desirable features of a particular peptide, e.g., an oligopeptide, once such peptide has been found, but that avoids the undesirable features, e.g., flexibility (loss of conformation) and bond breakdown are known as a "peptidomimetics". (See, e.g., Spatola, A. F. Chemistry and Biochemistry of Amino Acids. Peptides, and Proteins (Weistein, B, Ed.), Vol. 7, pp. 267–357, Marcel Dekker, New York (1983), which describes the use of the methylenethio bioisostere [$CH_2 S$] as an amide replacement in enkephalin analogues; and Szelke et al., In peptides: Structure and Function, Proceedings of the Eighth American Peptide Symposium, (Hruby and Rich, Eds.); pp. 579–582, Pierce Chemical Co., Rockford, Ill. (1983), which describes renin inhibitors having both the methyleneamino [$CH_2 NH$] and hydroxyethylene [$CHOHCH_2$] bioisosteres at the Leu-Val amide bond in the 6-13 octapeptide derived from angiotensinogen).

In general, the design and synthesis of a peptidomimetic involves starting with the sequence of the peptide and the conformation data (e.g., geometry data, such as bond lengths and angles) of a desired peptide (e.g., the most probable simulated peptide), and using such data to determine the geometries that should be designed into the peptidomimetic. Numerous methods and techniques are known in the art for performing this step, any of which could be used. (See, e.g., Farmer, P. S., *Drug Design*, (Ariens, E. J. ed.), Vol. 10, pp. 119–143 (Academic Press, New York, London, Toronto, Sydney and San Francisco) (1980); Farmer, et al., in TIPS, 9/82, pp. 362–365; Verber et al., in TINS, 9/85, pp. 392–396;

Kaltenbronn et al., in *J. Med. Chem.* 33: 838–845 (1990); and Spatola, A. F., in *Chemistry and Biochemistry of Amino Acids. Peptides, and Proteins*, Vol. 7, pp. 267–357, Chapter 5, "Peptide Backbone Modifications: A Structure-Activity Analysis of Peptides Containing Amide Bond Surrogates. Conformational Constraints, and Relations" (B. Weisten, ed.; Marcell Dekker: New York, pub.) (1983); Kemp, D. S., "Peptidomimetics and the Template Approach to Nucleation of β-sheets and α-helices in Peptides," Tibech, Vol. 8, pp. 249–255 (1990). Additional teachings can be found in U.S. Pat. Nos. 5,288,707; 5,552,534; 5,811,515; 5,817,626; 5,817,879; 5,821,231; and 5,874,529.

In one approach, a three-dimensional structure of a protein of interest (e.g., the Pro385 or Ser385 polypeptide or fragment thereof) is determined by x-ray crystallography, NMR, or neutron diffraction and computer modeling. Useful protein models of Pro385 or Ser385 can also be gained by computer modeling alone, as explained in Examples 3, 4, and 5. These models are compared to peptide and chemical libraries using computer software that allows one to analyze interactions between the modeled receptor and the candidate ligand. A number of articles review computer modelling of drugs interactive with specific-proteins, such as Rotivinen, et al., 1988, Acta Pharmaceutical Fennica 97:159–166; Ripka, New Scientist 54–57 (Jun. 16, 1988); McKinaly and Rossmann, 1989, Annu. Rev. Pharmacol. Toxiciol. 29:111–122; Perry and Davies, OSAR: Quantitative Structure-Activity Relationships in Drug Design pp. 189–193 (Alan R. Liss, Inc. 1989); Lewis and Dean, 1989 Proc. R. Soc. Lond. 236:125–140 and 141–162; and, with respect to a model receptor for nucleic acid components, Askew, et al., 1989, J. Am. Chem. Soc. 111:1082–1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario).

In addition, the peptide of interest (e.g., Pro385 or Ser385 $GABA_A$ α6) can be analyzed by an alanine scan (Wells, *Methods in Enzymol.* 202:390–411 (1991). In this technique, an amino acid residue is replaced by alanine, and its affect on the peptide's activity is measured by a functional assay, such as described in Example 15. Each of the amino acid residues of the peptide is analyzed in this manner and the important regions of the peptide are identified. Subsequently, this functionally important region is recorded on a computer readable medium, stored in a first database in a computer system, and a search program is employed, as described in Examples 3, 4, 5, and below, to generate a protein model of the functionally important region. Once a protein model has been generated, a second database comprising one or more libraries having peptides, chemicals, peptidomimetics and other agents which interact with proteins, is accessed by a search program and individual agents are compared to the protein model to identify agents which interact with the functionally important region of the Pro385 or Ser385 $GABA_A$ α6 protein. Interacting agents identified by the approach above are then tested in assays that monitor ion transport as described in Example 15.

It is also possible to isolate a target-specific antibody, selected by a functional assay, and then to solve its crystal structure. In principal, this approach yields a pharmacore upon which subsequent drug design can be based. By this approach, protein crystallography of Pro385 or Ser385 $GABA_A$ α6 is by-passed altogether by generating anti-idiotypic antibodies (anti-ids) to a functional, pharmacologically active antibody. As a mirror image of a mirror image, the binding site of the anti-ids would be expected to be an analog of a region of the Pro385 or Ser385 $GABA_A$ α6 protein. The anti-id could then be used to identify and isolate peptides, peptidomimetics and chemicals from libraries of such compounds known to those in the art. Selected peptides, peptidomimetics and chemicals would then act as the pharmacore. Thus, one can design drugs which have transport inhibition activity, which differentially interact at Pro385 and Ser385, or which bypass the Pro385 or Ser385 $GABA_A$ α6 protein altogether.

Many computer programs and databases can be used with embodiments of the invention. The following list is intended not to limit the invention but to provide guidance to programs and databases which are useful with the nucleic acid and protein sequence embodiments of the present invention. The programs and databases which can be used include, but are not limited to: McPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, *J. Mol. Biol.* 215: 403 (1990)), FASTA (Pearson and Lipman, *Proc. Natl. Acad. Sci. USA*, 85: 2444 (1988)), Catalyst (Molecular Simulations Inc.), Catalyst/SHAPE (Molecular Simulations Inc.), $Cerius^2$.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), Modeller 4 (Sali and Blundell J. Mol. Biol. 234:217–241 (1997)), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), the EMBL/Swissprotein database, the MDL Available Chemicals Directory database, the MDL Drug Data Report data base, the Comprehensive Medicinal Chemistry database, Derwents's World Drug Index database, and the BioByteMasterFile database. Many other programs and data bases would be apparent to one of skill in the art given the present disclosure. Example 7 describes the preparation of PCR primers and the amplification of Pro385 or Ser385 $GABA_A$ α6 DNA.

EXAMPLE 7

The probes of the invention can correspond to any region of Pro385 or Ser385 so long as the codon encoding the proline or serine residue at position 385 is present. The Pro385 or Ser385 $GABA_A$ α6 probes are generally at least 10 bases, and preferably at least 12, 15, or 17 bases in length. More preferably, the Pro385Ser probes are at least 20–30 bases in length. In some embodiments, the Pro385 or Ser385 $GABA_A$ α6 probes can be more than 30 bases in length.

Probes derived from nucleic acids encoding Pro385 or Ser385 $GABA_A$ α6, or portions thereof can be labeled with detectable signals familiar to those skilled in the art, including radioisotopes and non-radioactive labels, to provide a detectable probe. The detectable probe can be single stranded or double stranded and can be made using techniques known in the art, including in vitro transcription, nick translation, or kinase reactions. A nucleic acid sample containing a sequence capable of hybridizing to the labeled probe is contacted with the labeled probe. If the nucleic acid in the sample is double stranded, it can be denatured prior to contacting the probe. In some applications, the nucleic acid sample can be immobilized on a surface such as a nitrocellulose or nylon membrane. The nucleic acid sample can comprise nucleic acids obtained from a variety of sources, including genomic DNA, cDNA libraries, RNA, or biological samples. A biological sample is understood to mean a sample obtainable from a human having nucleated cells comprising nucleic acid. A biological sample in the context of the invention, for example, can be a blood sample drawn by venipuncture of a finger prick, or a swab contacted to the inner cheek of a human whereby epithelial cells are collected.

Procedures used to detect the presence of nucleic acids capable of hybridizing to the detectable probe include well known techniques such as Southern blotting, Northern blotting, dot blotting, colony hybridization, and plaque hybridization. In some applications, the nucleic acid capable of hybridizing to the labeled probe can be cloned into vectors such as expression vectors, sequencing vectors, or in vitro transcription vectors to facilitate the characterization and expression of the hybridizing nucleic acids in the sample. For example, such techniques can be used to isolate and clone sequences in a genomic library or cDNA library which are capable of hybridizing to the detectable probe. Alternatively, the nucleic acids encoding Pro385 or Ser385 $GABA_A$ α6 are manipulated using conventional techniques in molecular biology to create recombinant constructs that express Pro385 or Ser385 $GABA_A$ α6 polypeptide. Example 8 provides several approaches to synthesize, express, and isolate or purify the Pro385 or Ser385 $GABA_A$ α6 protein, or fragments thereof.

EXAMPLE 8

To express the proteins encoded by Pro385 or Ser385 $GABA_A$ α6, or portion thereof, nucleic acids containing the coding sequence for the proteins or portions thereof are obtained and cloned into a suitable expression vector such that the coding region is operably linked to a heterologous promoter. The nucleic acid can, for example, encode a polypeptide comprising at least 3, 6 or 10 consecutive amino acids of the sequence deduced from SEQ ID NO: 11 or 12. In some embodiments, the nucleic acid can encode a polypeptide comprising at least 15 consecutive amino acids of the sequence deduced from SEQ ID NO: 11 or 12. In other embodiments, the nucleic acid can encode a polypeptide comprising at least 25 consecutive amino acids of the sequence of SEQ ID NO: 11 or 12. In other embodiments, the nucleic acid can encode a polypeptide comprising at least 60, at least 75, at least 100 or more than 100 consecutive amino acids of the sequence deduced from SEQ ID No: 11 or 12. Still further, in other embodiments, the nucleic acid can encode the entire coding region of Pro385 or Ser385 $GABA_A$ α6 and have a molecular weight of about 50 kD in 10% SDS PAGE.

The nucleic acid encoding the protein or polypeptide to be expressed is operably linked to a promoter in an expression vector using conventional cloning technology. The expression vector can be any of the mammalian, yeast, insect, parasite, or bacterial expression systems known in the art. Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). If desired, to enhance expression and facilitate proper protein folding, the codon context and codon pairing of the sequence can be optimized for the particular expression organism in which the expression vector is introduced, as explained by Hatfield, et al., U.S. Pat. No. 5,082,767, incorporated herein by this reference. Further, a secretory leader sequence can be incorporated so as to facilitate purification of the protein. Many vectors or recombinant constructs having Pro385 or Ser385 $GABA_A$ α6 nucleic acid sequence (full-length or portion thereof) which enable Pro385 or Ser385 $GABA_A$ α6 protein expression are contemplated.

The following is provided as one possible method to express the proteins encoded by the nucleic acids described above. First, the methionine initiation codon for the gene and the poly A signal of the gene are identified. If the nucleic acid encoding the polypeptide to be expressed lacks a methionine to serve as the initiation site, an initiating methionine can be introduced next to the first codon of the nucleic acid using conventional techniques. Similarly, if the Pro385 or Ser385 $GABA_A$ α6 cDNA lacks a poly A signal, this sequence can be added to the construct by, for example, splicing out the Poly A signal from pSG5 (Stratagene) using BglI and SalI restriction endonuclease enzymes and incorporating it into the mammalian expression vector pXT1 (Stratagene). pXT1 contains the LTRs and a portion of the gag gene from Moloney Murine Leukemia Virus. The position of the LTRs in the construct allow efficient stable transfection. The vector includes the Herpes Simplex Thymidine Kinase promoter and the selectable neomycin gene.

The nucleic acid encoding the polypeptide to be expressed can be obtained by PCR from the bacterial vector using oligonucleotide primers complementary to the nucleic acid and containing restriction endonuclease sequences for Pst I incorporated into the 5'primer and BglII at the 5' end of the corresponding cDNA 3' primer, taking care to ensure that the nucleic acid is positioned in frame with the poly A signal. The purified fragment obtained from the resulting PCR reaction is digested with PstI, blunt ended with an exonuclease, digested with Bgl II, purified and ligated to pXT1, now containing a poly A signal and digested with BglII. The ligated product is transfected into a suitable cell line, e.g., mouse NIH 3T3 cells, using Lipofectin (Life Technologies, Inc., Grand Island, N.Y.) under conditions outlined in the product specification. Positive transfectants are selected after growing the transfected cells in 600 ug/ml G418 (Sigma, St. Louis, Mo.). Preferably the expressed protein is released into the culture medium, thereby facilitating purification.

Alternatively, the Pro385 or Ser385 $GABA_A$ α6 nucleic acid, or portion thereof can be cloned into pED6dpc2 as described above. The resulting pED6dpc2 constructs can be transfected into a host cell, such as COS 1 cells. Methotrexate resistant cells are selected and expanded. Preferably, the protein expressed from the extended cDNA is released into the culture medium thereby facilitating purification.

Another embodiment contemplated by the present inventors utilizes the "Xpress system for expression and purification" (Invitrogen, San Diego, Calif.). The Xpress system is designed for high-level production and purification of recombinant proteins from bacterial, mammalian, and insect cells. The Xpress vectors produce recombinant proteins fused to a short N-terminal leader peptide which has a high affinity for divalent cations. Using a nickel-chelating resin (Invitrogen), the recombinant protein can be purified in one step and the leader can be subsequently removed by cleavage with enterokinase.

One vector for the expression of Pro385 or Ser385 $GABA_A$ α6 polypeptide is the pBlueBacHis2 Xpress. The pBlueBacHis2 Xpress vector is a Baculovirus expression vector containing a multiple cloning site, an ampicillin resistance gene, and a lac z gene. By one approach, the Pro385 or Ser385 GABA$_A$ α6 nucleic acid, or portion thereof is cloned into the pBlueBacHis2 Xpress vector and SF9 cells are infected. The expression protein is then isolated and purified according to the maufacturer's instructions. Several other cultured cell lines having recombinant constructs or vectors comprising Pro385 or Ser385 GABA$_A$ α6 sequence or portions thereof are embodiments of the present invention and their manufacture would be routine given the present disclosure.

Proteins in the culture medium are also separated by gel electrophoresis. The separated proteins are then detected using techniques such as Coomassie or silver staining or using antibodies against the protein. Coomassie and silver staining techniques are familiar to those skilled in the art.

If desired, the proteins can be ammonium sulfate precipitated or separated based on size or charge prior to electrophoresis. The protein encoded by the Pro385 or Ser385 GABA$_A$ α6 gene, Pro385 or Ser385 GABA$_A$ α6 cDNA, or portion thereof can also be purified using standard immunochromatography techniques. In such procedures, a solution containing the protein, such as the culture medium or a cell extract, is applied to a column having antibodies against the secreted protein attached to the chromatography matrix. The secreted protein is allowed to bind the immunochromatography column. Thereafter, the column is washed to remove non-specifically bound proteins. The specifically bound secreted protein is then released from the column and recovered using standard techniques.

If antibody production is undesirable, Pro385 or Ser385 GABA$_A$ α6 nucleic acid or portion thereof can be incorporated into expression vectors designed for use in purification schemes employing chimeric polypeptides. In such strategies the coding sequence of the Pro385 or Ser385 GABA$_A$ α6 nucleic acid or portion thereof is inserted in frame with the gene encoding the other half of the chimera. The other half of the chimera can be β-globin or a nickel binding polypeptide encoding sequence. A chromatography matrix having antibody to β-globin or nickel attached thereto is then used to purify the chimeric protein. Protease cleavage sites can be engineered between the β-globin gene or the nickel binding polypeptide and the Pro385 or Ser385 GABA$_A$ α6 cDNA such as enterokinase. Thus, the two polypeptides of the chimera can be separated from one another by protease digestion.

One useful expression vector for generating β-globin chimerics is pSG5 (Stratagene), which encodes rabbit β-globin. Intron II of the rabbit β-globin gene facilitates splicing of the expressed transcript, and the polyadenylation signal incorporated into the construct increases the level of expression. These techniques as described are well known to those skilled in the art of molecular biology. Standard methods are published in methods texts such as Davis et al., (*Basic Methods in Molecular Bioloy*, L. G. Davis, M. D. Dibner, and J. F. Battey, ed., Elsevier Press, NY, 1986) and many of the methods are available from Stratagene, Life Technologies, Inc., or Promega. Polypeptide can additionally be produced from the construct using in vitro translation systems such as the In vitro Express™ Translation Kit (Stratagene).

In addition to preparing and purifying Pro385 or Ser385 GABA$_A$ α6 polypeptide using recombinant DNA techniques, the Pro385 or Ser385 GABA$_A$ α6 polypeptides, fragments and/or derivatives thereof can be prepared by chemical synthesis methods (such as solid phase peptide synthesis) using methods known in the art such as those set forth by Merrifield et al., J. Am. Chem. Soc. 85:2149 (1964), Houghten et al., Proc. Natl. Acad. Sci. USA, 82:51:32 (1985), and Stewart and Young (solid phase peptide synthesis, Pierce Chem Co., Rockford, Ill. (1984). Such polypeptides can be synthesized with or without a methionine on the amino terminus. Chemically synthesized Pro385 or Ser385 GABA$_A$ α6 polypeptides or fragments can be oxidized using methods set forth in these references to form disulfide bridges. The Pro385 or Ser385 GABA$_A$ α6 polypeptides or fragments can be employed as biologically active or immunological substitutes for natural, purified Pro385 or Ser385 GABA$_A$ α6 polypeptide in therapeutic and immunological processes. Following synthesis or expression and purification of the proteins encoded by the Pro385 or Ser385 GABA$_A$ α6 nucleic acid or portion therof, the purified proteins can be used to generate antibodies as described in Example 9.

EXAMPLE 9

By one approach, substantially pure Pro385 or Ser385 GABA$_A$ α6 protein or polypeptide is isolated from a transfected or transformed cell. The concentration of protein in the final preparation is adjusted, for example, by concentration on an Amicon filter device, to the level of a few micrograms/ml. Monoclonal or polyclonal antibody to the protein can then be prepared as follows:

Monoclonal antibody to epitopes of any of the peptides identified and isolated as described can be prepared from murine hybridomas according to the classical method of Kohler, G. and Milstein, C., *Nature* 256:495 (1975) or derivative methods thereof. Briefly, a mouse is repetitively inoculated with a few micrograms of the selected protein or peptides derived therefrom over a period of a few weeks. The mouse is then sacrificed, and the antibody producing cells of the spleen isolated. The spleen cells are fused in the presence of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, E., *Meth. Enzymol.* 70:419 (1980), and derivative methods thereof. Selected positive clones can be expanded and their monoclonal antibody product harvested for use. Detailed procedures for monoclonal antibody production are described in Davis, L. et al. *Basic Methods in Molecular Biology* Elsevier, New York. Section 21–2.

Polyclonal antiserum containing antibodies to heterogenous epitopes of a single protein can be prepared by immunizing suitable animals with the expressed protein or peptides derived therefrom described above, which can be unmodified or modified to enhance immunogenicity. Effective polyclonal antibody production is affected by many factors related both to the antigen and the host species. For example, small molecules tend to be less immunogenic than others and can require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis, J. et al. *J. Clin. Endocrinol. Metab.* 33:988–991 (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., Chap. 19 in: *Handbook of Experimental Immunology* D. Wier (ed) Blackwell (1973). Plateau concentration of antibody is usually in the range of 0.1 to 0.2 mg/ml of serum (about 12 $\mu$M). Affinity of the antisera for the antigen is determined by preparing competitive binding curves, as described, for example, by Fisher, D., Chap. 42 in: *Manual of Clinical Immunology*, 2d Ed. (Rose and Friedman, Eds.) Amer. Soc. For Microbiol., Washington, D.C. (1980).

Antibody preparations prepared according to either protocol are useful in quantitative immunoassays which determine concentrations of antigen-bearing substances in biological samples; they are also used semi-quantitatively or qualitatively (e.g., in diagnostic embodiments that identify the presence of Pro385Ser in biological samples). Example 10 describes a nucleic acid-based diagnostic method of the invention.

EXAMPLE 10

In one embodiment, "sample" DNA is isolated from a biological source, such as blood, from subjects in need of BZD therapy. A panel of PCR primers based on regions of the nucleic acid(s) encoding Pro385 or Ser385 $GABA_A$ $\alpha 6$ are then utilized to amplify DNA of approximately 100–700 bases in length from the DNA specimen. Preferably, the PCR primers span the regions in which the polymorphic variants were identified. As controls, wild-type sequences from control subjects are amplified. Each of the sample DNAs is then sequenced using standard techniques, and a simple comparison would identify the presence of the Ser385 allele and, thus, the subject's predilection to BZD insensitivity. The PCR primers used to identify the presence of Pro385Ser in the sample can also be incorporated into PCR tubes and packaged as a diagnostic kit. Although PCR is preferred, other amplification methods such as the Transcription Mediated Amplification process described in U.S. Pat. No. 5,399,491 also can be useful for practicing the invention. By using the diagnostics and the method presented above, an accurate identification of the amino acid at position 385 in the $\alpha 6$ subunit of the $GABA_A$ neurotransmitter receptor in a subject can be rapidly determined and the subject's predilection to BZD/ethanol insensitivity can be identified. Example 11 discloses hybridization methods that can be used to identify the presence of Pro385Ser in a biological sample.

EXAMPLE 11

In another embodiment, the procedure of Example 10 is repeated to obtain a panel of amplified sequences from a specimen. This PCR-generated DNA is then digested with one or a combination of restriction enzymes. Preferably, the PCR generated DNA is digested with restriction enzymes. Such enzymes are commercially available and known to those of skill in the art. Alternatively, provided that a sufficient amount of biological sample can be obtained, the DNA isolated from blood can be directly digested with restriction enzymes and assayed according to the following method.

After digestion, the resultant gene fragments are size separated on a polyacrylamide gel and transferred to nitrocellulose using electroblotting techniques well known to those with skill in the art. Alternatively, agarose gel electrophoresis and conventional Southern blotting can be employed. For a review of Southern blotting see Davis et al. (*Basic Methods in Molecular Biology*, 1986, Elsevier Press. pp 62–65).

A panel of probes based on the sequence of the nucleic acid encoding Pro385 or Ser385 $GABA_A$ $\alpha 6$ or portions thereof (having at least 10 bases), are radioactively or colorimetrically labeled using methods known in the art, such as nick translation or end labeling, and hybridized to the Southern blot using techniques known in the art (Davis et al., supra). Preferably, the probe comprises at least 12, 15, or 17 consecutive nucleotides from the extended cDNA (or genomic DNAs obtainable therefrom). More preferably, the probe comprises at least 20–30 consecutive nucleotides from the extended cDNA (or genomic DNAs obtainable therefrom). In some embodiments, the probe comprises more than 30 nucleotides from the nucleic acids encoding Pro385 or Ser385 $GABA_A$ $\alpha 6$, or portions thereof In other embodiments, the probe comprises at least 40, at least 50, at least 75, at least 100, at least 150, or at least 200 consecutive nucleotides from the nucleic acids encoding Pro385 or Ser385 $GABA_A$ $\alpha 6$, or portions thereof.

Many hybridization and washing conditions are known to those of skill in the art. By one approach, the nucleic acid probe is hybridized to the immobilized nucleic acid under the following conditions: 7% sodium dodecyl sulfate (SDS), 0.5M NaPO4 pH 7.0, 1 mM EDTA at 50° C.; and washing is performed with 1% SDS at 42° C. More specifically, the method described in Example 12 is used to identify an $\alpha 6$ polymorphism.

EXAMPLE 12

Two patients in need of benzodiazepine drug treatment are identified using diagnostic procedures that are familiar to those having ordinary skill in the art. A biological sample is then obtained, for instance, blood samples are drawn from the two patients, populations of nucleated blood cells are obtained by centrifugation and genomic DNA is isolated from the resulting cell samples using standard laboratory procedures.

Aliquots of the two DNA samples are then used as sources of templates in a standard PCR reaction employing primers having polynucleotide sequences given by SEQ ID NO: 9 and SEQ ID NO: 10. The resulting amplification products are digested with Fok I restriction endonuclease, the digestion products are separated on a polyacrylamide gel, and the resulting gel is stained with ethidium bromide, all according to standard laboratory techniques familiar to those having ordinary skill in the art.

Results from the electrophoretic separation indicate that the two patients have different $\alpha 6$ polymorphisms. The amplified DNA from the first patient is 365 bp in length and is not cleaved by the Fok I restriction endonuclease, thereby indicating that the first patient is characterized by the more common Pro385 $\alpha 6$ allele. Conversely, the amplified DNA from the second patient is cleaved into two fragments having lengths of 261 and 104 bp, respectively. This latter result indicates that the second patient possesses the Pro385Ser polymorphism, or the Ser 385 allele. These results also indicate that the two patients will be differentially sensitive to benzodiazepine drugs and ethanol. The patient having the Pro385 $\alpha 6$ allele is treated with diazepam. This patient is sensitive to the drug and exhibits improvement in symptoms treatable by benzodiazepine drug therapy. The finding that the second patient carries the Ser 385 allele indicates that the patient will be less sensitive to benzodiazepine drug therapy. Accordingly, a medication other than a benzodiazepine drug is prescribed for the second patient. A rapid method to detect the Pro385 or Ser385 $GABA_A$ $\alpha 6$ nucleic acid sequence in a sample of DNA is provided in Example 13.

EXAMPLE 13

Another technique for identifying the presence of Ser385 and Pro385, or portions thereof, utilizes a dot blot hybridization technique. As above, DNA is isolated, purified, or amplified from a biologic sample, preferably blood. Oligonucleotide probes of approximately 10–30 bp in length are synthesized that complement the nucleic acids encoding Pro385 or Ser385 $GABA_A$ α6, or portions thereof. The probes are used to hybridize to the genomic DNA through conditions known to those in the art but preferably in 7% sodium dodecyl sulfate (SDS), 0.5M NaPO4 pH 7.0, 1 mM EDTA at 50° C. and washing in 1% SDS at 42° C. The oligonucleotides are end labeled with $P^{32}$ using polynucleotide kinase (Pharmacia) and the dot blots are created by spotting the DNA from the sample onto nitrocellulose or the like using a vacuum dot blot manifold (BioRad, Richmond Calif.). The nitrocellulose filter containing the genomic sequences is baked or UV linked to the filter, prehybridized and hybridized with labeled probe using techniques known in the art (Davis et al. supra). The $^{32}P$ labeled DNA fragments can be sequentially hybridized with successively stringent conditions to detect minimal differences between the 30 bp sequence and the DNA. The appearance of radioactive spots on the membrane represents a positive hybridization and identification of the presence of nucleic acid encoding Pro385 or Ser385 $GABA_A$ α6. Example 14 provides several approaches that can be used to create a multimeric support having Pro385 or Ser385 $GABA_A$ α6 or polypeptide fragments thereof.

EXAMPLE 14

A multimeric support comprising Pro385 or Ser385 $GABA_A$ α6 or polypeptides thereof can be obtained by coupling the protein, or polypeptide fragment, to a macromolecular support. A "support" can also be termed a carrier, a resin or any macromolecular structure used to attach or immobilize a protein or polypeptide fragment. In many embodiments, a liposome or lipid bilayer (natural or synthetic) is contemplated as a support. The macromolecular support can have a hydrophobic surface that interacts with the hydrophobic regions of the protein, or polypeptide fragment, by hydrophobic non-covalent interaction. The hydrophobic surface of the support can also be a polymer such as plastic or any other polymer in which hydrophobic groups have been linked such as polystyrene, polyethylene or polyvinyl. Alternatively, Pro385 or Ser385 $GABA_A$ α6 protein, or polypeptide fragment thereof, can be covalently bound to carriers including proteins and oligo/polysaccharides (e.g. cellulose, starch, glycogen, chitosane or aminated sepharose). In these later embodiments, a reactive group on the Pro385 or Ser385 $GABA_A$ α6 protein, or polypeptide fragment thereof, such as a hydroxy or amino, can be used to join to a reactive group on the carrier so as to create the covalent bond. Further, the support can comprise an inorganic carrier such as silicon oxide material (e.g. silica gel, zeolite, diatomaceous earth or aminated glass) to which the Pro385 or Ser385 $GABA_A$ α6, or polypeptide fragments thereof, is covalently linked through a hydroxy, carboxy, or amino group and a reactive group on the carrier.

We further contemplate that the incorporation of linkers or spacers, such as lambda linkers, between the Pro385 or Ser385 $GABA_A$ α6 protein, or polypeptide fragment and the support can be advantageous. The insertion of lambda linkers of an appropriate length can encourage greater flexibility in the molecule and can overcome steric hindrance which can occur when the protein is bound to the support. The determination of an appropriate length of linker that allows for the optimal binding of ligand to the multimeric Pro385 or Ser385 $GABA_A$ α6 protein, or polypeptide fragments thereof, can be determined without undue experimentation. Example 15 provides several high throughput screening methods that are used to identify agents that interact with Pro385 or Ser385 $GABA_A$ α6 protein or polypeptide fragments thereof.

EXAMPLE 15

One approach developed for labeling functional ion channels is based on the physical flow of conducting ions through the channel of interest. For one pico amp of ionic current, roughly $10^6$ ions \s pass can through an ion channel. By utilizing the property of monovalent thallium ($T(I^+)$) ions to crystallize at very low concentration with halide ions, such as $Br^-$, functional ion channels can be labeled. Operationally, once thallium ions are applied to one side of the membrane, they will pass through the channel pores, create a local increase in thallium concentration, and eventually crystallize with Br ions that are present on the other side of the membrane. The crystals grow to a visible size and thus mark the location of ion channels on the membrane (see, e.g., Lopatin et al., *Biophysical Journal* 74:2159–2170 (1998)).

In one aspect of the invention, a first group of xenopus oocytes are injected with roughly 5 ng of Ser385 $GABA_A$ α6 cRNA into the animal (dark) hemisphere (pole) and a measurement of oocyte current and membrane potential are recorded so as to provide a baseline value. As a control, the current and membrane potential of a second group xenopus oocytes that have been injected with roughly 5 ng of Pro385 cRNA is measured. The two groups of ooctyes are then injected with roughly 50 nl of 30 mM KBr, so as to bring the intracellular concentration of KBr to roughly 3 mM, and voltage-clamped with a 2-microelectrode voltage clamp in a thallium-containing solution. 40×410 ms linear voltage ramps from −80 mV to +50 mV are then applied at a frequency of 0.75 Hz to drive the inward flow of thallium ions and the ionic currents are recorded. The two groups of oocytes are then photographed. Multiple white crystals will be visible by light microscope on the animal hemisphere if the Pro385 or Ser385 $GABA_A$ α6 expressing oocytes allow for ion transport. By comparing the relative abilities of the two groups of oocytes to crystalize thalium, one of skill in the art can easily determine the extent to which the Pro385 or Ser385 $GABA_A$ α6 protein function as an ion transporter. Additionally, the crystalization assay described above can be performed in a multi-well format and libraries of agents, such as peptides, peptidomimetics, and chemicals can be screened for their ability to interfere with the level of ion transport potentiated by the Pro385 or Ser385 $GABA_A$ α6 protein. In this manner, agents, particularly BZD drugs and related compounds, can be rapidly screened for their ability to interact with the Pro385 or Ser385 $GABA_A$ α6 protein and modulate ion transport.

In an alternative method, liposomes having the Pro385 or Ser385 $GABA_A$ α6 protein are loaded with bromine ions ($Br^-$). Subsequently, the liposomes having the Pro385 or Ser385 $GABA_A$ α6 protein are contacted with thallium ions and electrical current is applied. The local increase in thallium concentration inside the liposome is detected by microscopic observation of crystals which form at the location of the ion channels. By comparing the relative abilities of Pro385 or Ser385 $GABA_A$ α6 carrying liposomes to crystalize thalium, one of skill in the art can easily determine the extent to which Pro385 or Ser385 $GABA_A$ α6 function as an ion transporter. Additionally, the crystalization assay described above can be performed in a multi-well format and libraries of agents, such as peptides, peptidomimetics, and chemicals can be screened for their ability to modulate the ion transport potentiated by the Pro385 or Ser385 $GABA_A$ α6 protein.

To directly measure ion transport, an agarose-hemi-clamp technique based on the capacity of agarose to electrically conduct ions as well as free solution while obviating the bulk flow of ions is used. (See, e.g., Lopatin et al.) By this approach, oocytes expressing the Ser385 GABA$_A$ α6 protein and oocytes expressing the Pro385 protein are voltage-clamped in a TlC1 bath solution, and 2 microelectrodes are used to record ion currents. Subsequently, the clamp circuit is switched off, the electrodes are removed, and the cell is completely embedded in 1% agar in the TlC1 solution. After the agar is set and cooled to room temperature, the piece of gel containing the cell is cut out and the cell is voltage-clamped again. By comparing the relative abilities of the oocytes expressing Pro385 GABA$_A$ α6 and the ocytes expressing Ser385 GABA$_A$ α6 to conduct electricity, one of skill in the art can easily determine the extent to which Pro385 and Ser385 GABA$_A$ α6 function as an ion transporter. Additionally, the agarose-hemi-clamp technique described above can be performed in a multi-well format and libraries of agents, such as peptides, peptidomimetics, and chemicals can be screened for their ability to modulate the ion transport potentiated by the Pro385 or Ser385 GABA$_A$ α6 protein.

By an alternative approach, multimeric supports having attached the Pro385 or Ser385 GABA$_A$ α6 protein, or polypeptide fragments thereof, are employed and impedance analysis of ion transport through the immobilized Pro385 or Ser385 GABA$_A$ α6 protein is determined. (Steinem et al., *Bioelectro Chemistry and Bioenergetics*, 42:213–220, (1997)).

In this embodiment, two types of multimeric supports are constructed by reconstituting the Pro385 or Ser385 GABA$_A$ α6 wild-type proteins into large unilamellar vesicles (LUV) of dimethyldioctadecylammoniumbromide (DODAB) which are then fused onto a negatively charged monolayer of 3-mercaptopropionic acid (MPA). An initial determination of impedance in the presence of different monovalant cations at varying concentrations is then made for the two types of multimeric supports. A.C. impedance spectroscopy, as an integral electrochemical method, is used because it offers the possibility to determine the electric parameters of thin films such as biomembranes without redoxactive marker ions. Thus, ions that permeate the membrane exhibit a resistance parallel to the membrane capacitance and in series to the capacitance of the substrate.

A.C. impedance analysis is performed using an SI 1260 impedance gain/phase analyzer from Solartron Instruments (Great Britain) controlled by a personal computer, however, those of skill in the art would be able to use other A.C. impedance analyzers. To prepare the Pro385 or Ser385 GABA$_A$ α6 multimeric support, gold electrodes are exposed for about 10 minutes to a 10 mM solution of the MPA so as to form a highly oriented self-assembled monolayer. Afterwards, the electrodes are rinsed extensively with a Tris buffer solution pH 8.6 to remove any remaining physisorbed molecules. To control the surface coverage and, therefore, the quality of the film, each step is monitored by impedance spectroscopy. A capacitance of about 9 mM F/cm$^2$ is a reference value for a successfully deposited monolayer.

Large unilamellar vesicles (LUV) of DODAB (1.5 mg/ml) with 1 mol % Pro385 or Ser385 GABA$_A$ α6 are prepared by a method of extrusion in the same buffer solution, as known by those of skilled in the art. (Steinem et al., *Biochim. Biophys. Acta* 1279:169–180 (1996)). The LUV vesicles are added to the prepared MPA monolayer in the electrochemical cell. A bilayer is formed at room temperature without stirring the solution. After one hour, the process is finished and the vesicle suspension is replaced by pure buffer.

The formation of the solid supported bilayer is then observed by impedance spectroscopy and measurements are taken in the absence of ions. Subsequently, impedance measurements are taken in the presence of different concentrations of LiCl, NaCl, KCl, and CsCl. After addition of different concentrations of one kind of ion to the DODAB bilayer, the solution is replaced by pure buffer and an impedance spectrum is recorded in order to ensure that the solid supported bilayer was not disrupted. The extent to which the Pro385 or Ser385 GABA$_A$ α6 protein has the ability to transport the particular ion will be ascertainable given that the impedance of the electrochemical system decreases significantly as the concentration of the ion increases.

Similar to the methods described above, a high throughput system can be designed to screen libraries of compounds or agents which would interact with Pro385 or Ser385 GABA$_A$ α6 and modulate ion transport. In essence, the approach above is scaled up and impedance spectroscopy is performed on multiple measuring chambers each having a set of working electrodes. Impedance measurements are taken before the addition of the agent from the library of peptides, peptidomimetics, and chemicals so that a baseline reading for a particular ion is determined. Once the baseline is recorded, different agents are added to each measuring chamber and impedance measurements are again recorded. Agents which interact with the Pro385 or Ser385 GABA$_A$ α6 protein and effect ion transport are then identified according to the relative change in impedance in the presence of the agent. That is, an increase in the impedance of the electrical system when the agent is present, as compared to its absence, for example, will indicate that the compound interferes with the ability of the Pro385 or Ser385 GABA$_A$ α6 protein to transport the ion.

Although the invention has been described with reference to embodiments and examples, it should be understood that various modifications can be made without departing from the spirit of the invention. Accordingly, the invention is limited only by the following claims. All references cited herein are hereby expressly incorporated by reference.

What is claimed is:

1. An isolated polynucleotide encoding the α6 subunit of the human GABA$_A$ neurotransmitter receptor, wherein said polynucleotide has a codon for amino acid position 385 of said α6 polypeptide sequence, wherein said codon encodes a serine residue.

2. The isolated polynucleotide of claim 1, wherein said polynucleotide comprises SEQ ID NO: 12.

3. The isolated polynucleotide of claim 1 having said codon, wherein said polynucleotide comprises at least 10 consecutive bases of SEQ ID NO: 12.

4. The isolated polynucleotide of claim 1 having said codon, wherein said polynucleotide comprises at least 10 consecutive bases that hybridize to SEQ ID NO: 12 or a sequence complementary thereto under the following conditions: 7% sodium dodecyl sulfate (SDS), 0.5M NaPO4 pH 7.0, 1 mM EDTA at 50° C.; and washing with 1% SDS at 42° C.

* * * * *

SEQUENCE LISTING

<160> NUMBER OF SEQ ID NOS: 14

<210> SEQ ID NO 1
<211> LENGTH: 20
<212> TYPE: DNA
<213> ORGANISM: Human

<400> SEQUENCE: 1

-continued

```
atggcgtcat ctctgccctg                                            20

<210> SEQ ID NO 2
<211> LENGTH: 20
<212> TYPE: DNA
<213> ORGANISM: Human

<400> SEQUENCE: 2
ctccaaatcc cggccgcagc                                            20

<210> SEQ ID NO 3
<211> LENGTH: 20
<212> TYPE: DNA
<213> ORGANISM: Human

<400> SEQUENCE: 3
ggactgatga gaggttgaag                                            20

<210> SEQ ID NO 4
<211> LENGTH: 20
<212> TYPE: DNA
<213> ORGANISM: Human

<400> SEQUENCE: 4
catggtgtat aaaatggttc                                            20

<210> SEQ ID NO 5
<211> LENGTH: 20
<212> TYPE: DNA
<213> ORGANISM: Human

<400> SEQUENCE: 5
gtgaatacgt tataatgaca                                            20

<210> SEQ ID NO 6
<211> LENGTH: 18
<212> TYPE: DNA
<213> ORGANISM: Human

<400> SEQUENCE: 6
caaaaacagt tcttgctg                                              18

<210> SEQ ID NO 7
<211> LENGTH: 20
<212> TYPE: DNA
<213> ORGANISM: Human

<400> SEQUENCE: 7
ggatcaccac tgttttaact                                            20

<210> SEQ ID NO 8
<211> LENGTH: 20
<212> TYPE: DNA
<213> ORGANISM: Human

<400> SEQUENCE: 8
agtagctttt gatattgtca                                            20

<210> SEQ ID NO 9
<211> LENGTH: 20
<212> TYPE: DNA
<213> ORGANISM: Human

<400> SEQUENCE: 9
```

```
ctgactccaa atatcatctg                                               20

<210> SEQ ID NO 10
<211> LENGTH: 20
<212> TYPE: DNA
<213> ORGANISM: Human

<400> SEQUENCE: 10
gagaagcatc tacacaagtc                                               20

<210> SEQ ID NO 11
<211> LENGTH: 365
<212> TYPE: DNA
<213> ORGANISM: Human

<400> SEQUENCE: 11
ctgactccaa atatcatctg aagaaaagga tcacttctct gtctttgcca atagtttcat   60
cttccgaggc caataaagtg ctcacgagag cgcccatctt acaatcaaca cctgtcacac  120
ccccaccact cccgccagcc tttggaggca ccagtaaaat agaccagtat tctcgaattc  180
tcttcccagt tgcatttgca ggattcaacc ttgtgtactg ggtagtttat ctttccaaag  240
atacaatgga agtgagtagc agtgttgaat agcttttcca ggacaacctg aattctataa  300
gttcttgttt tctgtttcct atgttttctt aaaaaatagc attgagactt gtgtagatgc  360
ttctc                                                              365

<210> SEQ ID NO 12
<211> LENGTH: 365
<212> TYPE: DNA
<213> ORGANISM: Human

<400> SEQUENCE: 12
ctgactccaa atatcatctg aagaaaagga tcacttctct gtctttgcca atagtttcat   60
cttccgaggc caataaagtg ctcacgagag cgcccatctt acaatcaaca cctgtcacat  120
ccccaccact cccgccagcc tttggaggca ccagtaaaat agaccagtat tctcgaattc  180
tcttcccagt tgcatttgca ggattcaacc ttgtgtactg ggtagtttat ctttccaaag  240
atacaatgga agtgagtagc agtgttgaat agcttttcca ggacaacctg aattctataa  300
gttcttgttt tctgtttcct atgttttctt aaaaaatagc attgagactt gtgtagatgc  360
ttctc                                                              365

<210> SEQ ID NO 13
<211> LENGTH: 233
<212> TYPE: DNA
<213> ORGANISM: Human

<400> SEQUENCE: 13
ggatcaccac tgttttaact atgaccactt tgagcatcag tgcccggcac tctttgccaa   60
aagtgtcata tgccactgcc atggattggt tcatagctgt ttgctttgca ttcgtcttct  120
ctgctcttat cgagttcgca gctgtcaact actttaccaa tcttcagaca cagaaggcga  180
aaaggaaggc acagtttgca gccccaccca cagtgacaat atcaaaagct act         233

<210> SEQ ID NO 14
<211> LENGTH: 233
<212> TYPE: DNA
<213> ORGANISM: Human
```

```
<400> SEQUENCE: 14
ggatcaccac tgttttaact atgaccactt tgagcatcag tgcccggcac tctttgccaa        60
aagtgtcata tgccactgcc atggattggt tcatagctgt ttgctttgca ttcgtcttct       120
ctgctcttat cgagttcgca gctgtcaact actttaccaa tcttcagaca cagaaggcca       180
aaaggaaggc acagtttgca gccccaccca cagtgacaat atcaaaagct act              233
```